US010131892B2

(12) United States Patent
Okuma et al.

(10) Patent No.: US 10,131,892 B2
(45) Date of Patent: Nov. 20, 2018

(54) THERMOSTABLE CELLOBIOHYDROLASE

(71) Applicant: HONDA MOTOR CO., LTD., Minato-ku, Tokyo (JP)

(72) Inventors: Jiro Okuma, Wako (JP); Migiwa Suda, Wako (JP); Asuka Yamaguchi, Wako (JP); Yoshitsugu Hirose, Wako (JP); Yasuhiro Kondo, Wako (JP); Masaru Sato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 33 days.

(21) Appl. No.: 15/063,941

(22) Filed: Mar. 8, 2016

(65) Prior Publication Data

US 2016/0264952 A1    Sep. 15, 2016

(30) Foreign Application Priority Data

Mar. 11, 2015   (JP) ................. 2015-048351

(51) Int. Cl.
*C12N 9/42* (2006.01)
*C12P 19/02* (2006.01)
*C12P 19/14* (2006.01)

(52) U.S. Cl.
CPC ............ *C12N 9/2437* (2013.01); *C12P 19/02* (2013.01); *C12P 19/14* (2013.01); *C12Y 302/01091* (2013.01)

(58) Field of Classification Search
CPC ........... C12Y 302/01091; C12N 9/2437; C12P 19/02; C12P 19/14
See application file for complete search history.

(56) References Cited

U.S. PATENT DOCUMENTS

2011/0207182 A1   8/2011   Sapra et al.

FOREIGN PATENT DOCUMENTS

| EP | 2287178 A2 | 2/2011 |
| JP | 64-063377 A | 3/1989 |
| WO | 00/39288 A1 | 7/2000 |
| WO | 2008066931 A2 | 6/2008 |
| WO | 2014/155566 A1 | 10/2014 |
| WO | 2014157492 A1 | 10/2014 |

OTHER PUBLICATIONS

Branden et al., Introduction to Protein Structure, Garland Publishing Inc., New York, p. 247.*
Witkowski et al., Biochemistry 38:11643-11650, 1999.*
Seffernick et al., J. Bacteriol. 183(8):2405-2410, 2001.*
Sadowski et al., Current Opinion in Structural Biology 19:357-362, 2009.*
Zverlov et al., Microbiology 144:457-465; 1998.*
Kanafusa-Shinkai et al., Journal of Bioscience and Bioengineering 115(1):64-70, 2013.*
Anonymous Author, "UPI0003432C49", internet article URL:http://www.uniprot.org/uniparc/UPI0003432C49, Apr. 13, 2012.
Anonymous Author, "UPI0004F8B81F", internet article URL:http://www.uniprot.org/uniparc/UPI0004F8B81F Sep. 23, 2014.
Anonymous Author, "EM_STD:JN225122", internet article URL:http://ibis/exam/dbfetch.jsp?id=EM_STD:JN225122, Jan. 2, 2014.
Search Report dated May 23, 2016 for corresponding European Patent Application No. 16159436.1.
Boisset, et al., "Imaging the Enzymatic Digestion of Bacterial Cellulose Ribbons Reveals the Endo Character of the Cellobiohydrolase Cel6A from Humicola insolens and Its Mode of Synergy with Cellobiohydrolase Cel7A", Applied and Environmental Microbiology, Apr. 2000, pp. 1444-1452, vol. 66, No. 4.
Ganju, et al., "Purification and characterization of two cellobiohydrolases from *Chaetomium thermophile* var. coprophile", Biochimica et Biophysics Acta, Dec. 8, 1989, pp. 266-274, vol. 993, No. 2, Elsevier.
Hong, et al., "Cloning of a gene encoding thermostable cellobiohydrolase from Thermoascus aurantiacus and its expression in yeast", Appl Microbiol Biotechnol, 2003, pp. 42-50, Springer-Verlag.
Irwin et al., "Cloning, expression and characterization of a Family 48 exocellulase, Cel48A, from Thermobifida fusca" Eur. J. Biochem., 2000, pp. 4988-4997.
Quinlan, et al., "Pyrobayes: an improved base caller for SNP discovery in pyrosequences", Nature Methods, Feb. 2008, pp. 179-181, vol. 5, No. 2, Nature Publishing Group.
Noguchi et al., "MetaGeneAnnotator: Detecting Species-Specific Patterns of Ribosomal Binding Site for Precise Gene Prediction in Anonymous Prokaryotic and Phage Genomes", NDA Research, 2008, pp. 387-396.
Finn et al., "The Pfam protein families database", Nucleic Acids Research Database, 2010, pp. D211-D222, vol. 38.
Durbin et al, Biological Sequence Analysis: Probabilistic models of proteins and nucleic acids, 1998, "The theory behind profile HMMs", Cambridge University Press.
Office Action issued in the corresponding Japanese Patent Application 2015-048351, with the English translation thereof, dated Sep. 18, 2018.

* cited by examiner

*Primary Examiner* — Delia M Ramirez
(74) *Attorney, Agent, or Firm* — Carrier Blackman & Associates, P.C.; Joseph P. Carrier; Fulchand P. Shende

(57) ABSTRACT

A thermostable cellobiohydrolase, having a cellobiohydrolase catalytic domain including: (A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of phosphoric acid swollen Avicel at least under conditions of 75° C. and pH 5.5, or (C) a polypeptide including an amino acid sequence having 75% or greater sequence identity with the amino acid sequence represented by SEQ ID NO: 1 or 2, and having hydrolysis activity against a substrate of phosphoric acid swollen Avicel at least under conditions of 75° C. and pH 5.5.

8 Claims, 5 Drawing Sheets

Specification includes a Sequence Listing.

*FIG. 1*

THERMOSTABLE CELLOBIOHYDROLASE

TECHNICAL FIELD

The present invention relates to a thermostable cellobiohydrolase, a polynucleotide encoding the thermostable cellobiohydrolase, an expression vector for expressing the thermostable cellobiohydrolase, a transformant into which the expression vector has been incorporated, and a method for producing a cellulose degradation product using the thermostable cellobiohydrolase.

Priority is claimed on Japanese Unpublished Patent Application No. 2015-048351, filed Mar. 11, 2015, the content of which is incorporated herein by reference.

BACKGROUND ART

In recent years, as a result of environmental problems such as global warming and atmospheric pollution, as well as concerns related to energy supplies for transportation, including the dramatic increase in the cost of crude oil and the expectation of depletion of crude oil sources in the near future (peak oil), the development of alternative energy sources to oil has become an extremely important issue. Plant biomass or lignocellulose is the most plentiful renewable energy source on earth, and holds great promise as an alternative energy source to oil. The main component of plant biomass dry weight is lignocellulose, which is composed of polysaccharides such as cellulose and hemicellulose, and lignin. For example, polysaccharides can be hydrolyzed by a glycoside hydrolase such as a cellulase or hemicellulase to form monosaccharides such as glucose and xylose, which can then be used as biofuels or the raw materials for chemical products.

Lignocellulose is recalcitrant due to its highly complex structure, and is difficult to degrade or hydrolyze with a single glycoside hydrolase. The complete hydrolysis of lignocellulose generally requires three types of enzymes, namely an endoglucanase (cellulase or endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21), and it is thought that the addition of a further plurality of enzymes including the hemicellulase xylanase (endo-1,4-β-xylanase, EC 3.2.1.8) and other plant cell wall-degrading enzymes such as β-xylosidase (EC 3.2.1.37) is also necessary.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 75° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. As a result, for all of the various glycoside hydrolases, the development of enzymes having superior thermal stability is very desirable.

When cellulose is hydrolyzed by a cellobiohydrolase, the disaccharide cellobiose is the main product. Cellobiohydrolases include some types which initiate hydrolysis from the reducing ends of cellulose (such as cellobiohydrolases belonging to the GH7 and GH48 families and the like), and some types which initiate hydrolysis from the non-reducing ends (such as cellobiohydrolases belonging to the GH5, GH6 and GH9 families and the like), and it is known that if the two types are used in combination, then the cellulose degradation activity is superior to that observed when either type is used alone (for example, see Non-Patent Document 1). Among cellobiohydrolases which initiate hydrolysis from the non-reducing ends of cellulose, a cellobiohydrolase of the GH6 family having an optimum temperature exceeding 75° C. has been reported (for example, see Patent Document 1).

However, in the case of cellobiohydrolases which initiate hydrolysis from the reducing ends, few enzymes of high thermal stability are known, although in the case of cellobiohydrolases belonging to the GH7 family, cellobiohydrolases have been isolated from the thermophilic filamentous fungi *Chaetomium thermophilum* (for example, see Non-Patent Document 2) and *Thermoascus aurantiacus* (for example, see Non-Patent Document 3) with optimum temperatures of 75° C. and 65° C. respectively. Further, in terms of cellobiohydrolases belonging to the GH48 family, Cel48A has been isolated from the thermophilic actinomycete *Thermobifida furca* (for example, see Non-Patent Document 4), and has an optimum temperature of about 60° C.

PRIOR ART LITERATURE

Patent Documents

Patent Document 1: International Patent Publication No. 2014/157492

Non-Patent Documents

Non-Patent Document 1: Boisset et al., Applied and Environmental Microbiology, 2000, vol. 66, pp. 1444 to 1452.
Non-Patent Document 2: Ganju et al., Biochimica et Biophysica Acta, 1989, vol. 993, pp. 266 to 274.
Non-Patent Document 3: Hong et al., Applied Microbiology and Biotechnology, 2003, vol. 63, pp. 42 to 50.
Non-Patent Document 4: Irwin et al., European Journal of Biochemistry, 2000, vol. 267, pp. 4988 to 4997.

SUMMARY OF THE INVENTION

Problems to be Solved by the Invention

The present invention has an object of providing a novel thermostable cellobiohydrolase belonging to the GH48 family, which exhibits cellobiohydrolase activity at least at 75° C., and at 80° C. in the presence of calcium ions, and also exhibits a synergistic effect with cellobiohydrolases of the GH6 family, as well as providing a polynucleotide encoding the thermostable cellobiohydrolase, an expression vector for expressing the thermostable cellobiohydrolase, a transformant into which the expression vector has been incorporated, and a method for producing a cellulose degradation product using the thermostable cellobiohydrolase.

Means for Solving the Problem

In order to achieve the above object, the inventors of the present invention extracted DNA directly from a compost culture, and by carrying out large-scale metagenomic sequencing of the microbial flora that was difficult to isolate, they succeeded in obtaining a thermostable cellobiohydrolase having a novel amino acid sequence, thus enabling them to complete the present invention.

In other words, a thermostable cellobiohydrolase, a polynucleotide, an expression vector, a transformant, a method for producing a thermostable cellobiohydrolase, a cellulase mixture, and a method for producing a cellulose degradation product according to the present invention have the aspects [1] to [12] described below.

[1] A thermostable cellobiohydrolase, having a cellobiohydrolase catalytic domain including:

(A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of phosphoric acid swollen Avicel at least under conditions of 75° C. and pH 5.5, or (C) a polypeptide including an amino acid sequence having 75% or greater sequence identity with the amino acid sequence represented by SEQ ID NO: 1 or 2, and having hydrolysis activity against a substrate of phosphoric acid swollen Avicel at least under conditions of 75° C. and pH 5.5.

[2] The thermostable cellobiohydrolase according to [1] which, in the presence of calcium ions, exhibits hydrolysis activity against a substrate of phosphoric acid swollen Avicel at least under conditions of 80° C. and pH 5.5.

[3] A polynucleotide, having a region encoding a cellobiohydrolase catalytic domain, the region including:

(a) a nucleotide sequence encoding a polypeptide including the amino acid sequence represented by SEQ ID NO: 1 or 2, (b) a nucleotide sequence encoding a polypeptide which includes an amino acid sequence in which at least one amino acid has been deleted, substituted, or added in the amino acid sequence represented by SEQ ID NO: 1 or 2, and has hydrolysis activity against a substrate of phosphoric acid swollen Avicel at least under conditions of 75° C. and pH 5.5, (c) a nucleotide sequence encoding a polypeptide which includes an amino acid sequence having 75% or greater sequence identity with the amino acid sequence represented by SEQ ID NO: 1 or 2, and has hydrolysis activity against a substrate of phosphoric acid swollen Avicel at least under conditions of 75° C. and pH 5.5, (d) a nucleotide sequence having 75% or greater sequence identity with a nucleotide sequence represented by SEQ ID NO: 3 or 4, and encoding a polypeptide that has hydrolysis activity against a substrate of phosphoric acid swollen Avicel at least under conditions of 75° C. and pH 5.5, or (e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of phosphoric acid swollen Avicel at least under conditions of 75° C. and pH 5.5.

[4] The polynucleotide according to [3], wherein the polypeptide also exhibits, in the presence of calcium ions, hydrolysis activity against a substrate of phosphoric acid swollen Avicel at least under conditions of 80° C. and pH 5.5.

[5] An expression vector incorporating the polynucleotide according to [3] or [4], the expression vector being capable of expressing a polypeptide having cellobiohydrolase activity in a host cell.

[6] A transformant into which the expression vector according to [5] has been introduced.

[7] The transformant according to [6], which is a eukaryote.

[8] A method for producing a thermostable cellobiohydrolase, the method including generating the thermostable cellobiohydrolase in the transformant according to [6] or [7].

[9] A glycoside hydrolase mixture, including the thermostable cellobiohydrolase according to [1] or [2], a thermostable cellobiohydrolase encoded by the polynucleotide according to [3] or [4], or a thermostable cellobiohydrolase produced by the method for producing a thermostable cellobiohydrolase according to [8], and at least one other glycoside hydrolase.

[10] The glycoside hydrolase mixture according to [9], including a GH6 family cellobiohydrolase.

[11] A method for producing a cellulose degradation product, the method including generating the cellulose degradation product by bringing a material containing cellulose into contact with the thermostable cellobiohydrolase according to [1] or [2], a thermostable cellobiohydrolase encoded by the polynucleotide according to [3] or [4], the transformant according to [6] or [7], a thermostable cellobiohydrolase produced by the method for producing a thermostable cellobiohydrolase according to [8], or the glycoside hydrolase mixture according to [9] or [10].

[12] The method for producing a cellulose degradation product according to [11], wherein the material containing cellulose is brought into contact with the thermostable cellobiohydrolase or the glycoside hydrolase mixture, and is also brought into contact with a GH6 family cellobiohydrolase.

Effects of the Invention

The thermostable cellobiohydrolase according to the present invention has cellobiohydrolase activity at least at 75° C. and pH 5.5, and at least at 80° C. and pH 5.5 in the presence of calcium ions. Moreover, the cellobiohydrolase activity of the thermostable cellobiohydrolase according to the present invention exhibits a synergistic effect with cellobiohydrolases of the GH6 family. For this reason, the thermostable cellobiohydrolase is suitable for hydrolysis processes of materials containing cellulose under high-temperature conditions.

Furthermore, the polynucleotide according to the present invention, an expression vector incorporating the polynucleotide, and a transformant into which the expression vector has been introduced can be used favorably in the production of the thermostable cellobiohydrolase according to the present invention.

BRIEF DESCRIPTION OF THE DRAWINGS

FIG. 1 is an alignment diagram of the amino acid sequence (SEQ ID NO: 2) of a cellobiohydrolase gene clone SD5AH4G-1D-1 and the amino acid sequence (SEQ ID NO: 9) of a cellulose 1,4-β-cellobiosidase of *Paenibacillus mucilaginosus*.

DETAILED DESCRIPTION OF THE INVENTION

[Thermostable Cellobiohydrolase]

Figure 2:
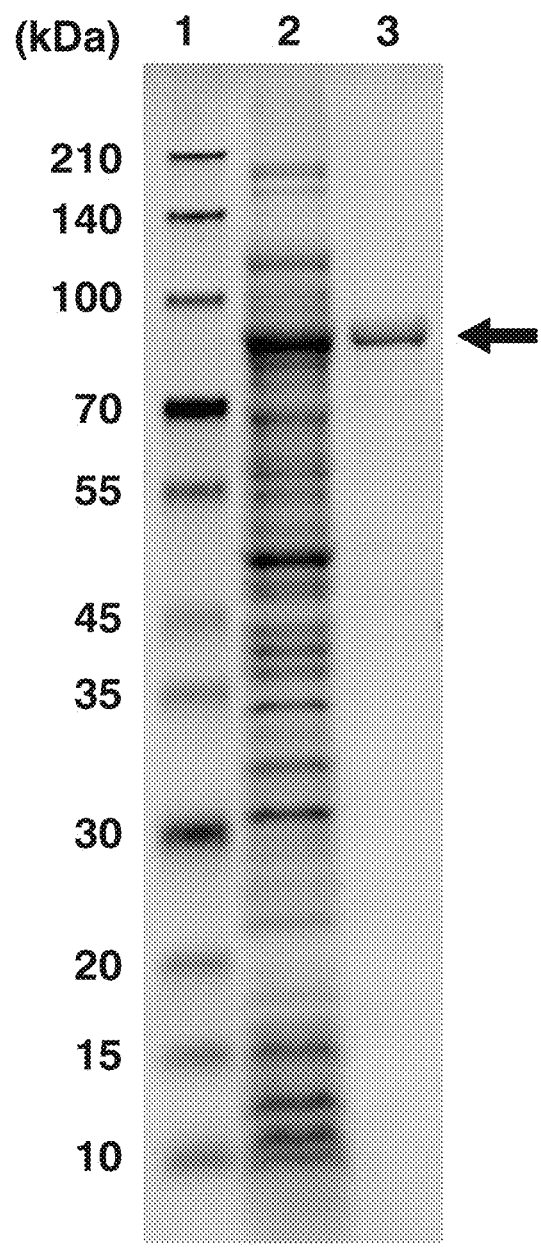
FIG. 2 is a diagram showing the SD5-PAGE analysis results of the SD5AH4G-ID-1 protein obtained by expressing the SD5AH4G-1D-1 gene in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that using current culturing techniques that target the isolation of microorganisms, a mere 0.1% or less of the microorganisms that exist in natural samples extracted from the natural world have been able to be isolated. This difficulty in culturing microorganisms is one of the reasons hindering the development of thermostable cellobiohydrolases. Accordingly, the development of thermostable cellobiohydrolases requires an approach that does not rely on conventional isolation and culturing techniques.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture. However, in compost samples, where the decomposition of organic matter is proceeding vigorously, a multitude of microorganisms exist, and even if a next generation giga sequencer is used, a larger amount of sequencing is still required to comprehensively sequence the genome. Accordingly, in order to more efficiently obtain the microbial flora having the targeted properties, the inventors of the present invention used a technique in which culturing was performed in a medium that used only cellulose as a carbon source.

As shown in Example 1 described below, the inventors of the present invention extracted the genomic DNA of microbial groups from compost cultures collected from locations in Japan, and conducted shotgun sequencing and annotation of the genomic DNA, thus obtaining open reading frames (ORFs) encoding amino acid sequences similar to those of known cellobiohydrolases. Primers were then designed based on the nucleotide sequence information of the obtained ORFs, and gene candidates were cloned from the genomic DNA of the compost cultures by the PCR method. The PCR-cloned DNAs were incorporated into *E. coli*, and proteins encoded by these nucleotide sequences were expressed and subjected to functional screening by phosphoric acid swollen Avicel (PSA) degradation activity assay. Finally, a thermostable cellobiohydrolase (hereafter also referred to as "SD5AH4G-1D-1") having PSA degradation activity was obtained from these ORFs. The amino acid sequence of SD5AH4G-1D-1 is represented by SEQ ID NO: 2, and the nucleotide sequence encoding the amino acid sequence of SD5AH4G-1D-1 is represented by SEQ ID NO: 4.

As shown below in Example 1 described below, SD5AH4G-1D-1 exhibits a high level of hydrolysis activity against PSA, and also exhibits weak hydrolysis activity against crystalline cellulose Avicel (2-hour reaction) and lichenan, which is composed of glucans having β-1,3 linkages and β-1,4 linkages, but exhibits almost no hydrolysis activity against other substrates. This substrate specificity suggests that SD5AH4G-1 D-1 is a glycoside hydrolase having cellobiohydrolase activity.

In the present description, the expression "cellobiohydrolase activity" means activity which produces cellobiose when a compound containing β-glycosidic linkages is used as a substrate, and the substrate is subjected to hydrolysis.

Examples of the "compound containing β-glycosidic linkages" include glucans having β-glycosidic linkages and oligosaccharides having β-glycosidic linkages.

Further, in the present description, the expression "has activity" or "exhibits activity" means that the enzyme acts against at least one substrate, with a significant difference occurring in the amount of reducing ends or the color development reaction of the hydrolyzed substrate compared with a negative control.

Accordingly, the expression "has cellobiohydrolase activity" means that the enzyme acts at least against substrates composed of compounds containing β-glycosidic linkages, and generates a significant difference in the amount of reducing ends or the color development reaction of the hydrolyzed substrate compared with a negative control.

Further, in another aspect, the expression "has cellobiohydrolase activity" means that the enzyme acts at least against a substrate of PSA, and preferably acts at least against substrates of PSA, Avicel and lichenan, and generates a significant difference in the amount of reducing ends or the color development reaction of the hydrolyzed substrate compared with a negative control.

When the amino acid sequence of SD5AH4G-1D-1 was searched against a database of known amino acid sequences, the amino acid sequence that showed the highest sequence identity was that of a cellulose 1,4-β-cellobiosidase belonging to the GH family 48 of *Paenibacillus mucilaginosus* (SEQ ID NO: 9), and the sequence identity (homology) in the GH48 catalytic domain was 73%. Based on the substrate specificity and the sequence identity of the amino acid sequence with that of known cellobiohydrolases, it was clear that SD5AH4G-1D-1 was a novel cellobiohydrolase belonging to the GH48 family.

SD5AH4G-1D-1 has cellobiohydrolase activity at least under conditions of 75° C. and pH 5.5. Actually, as shown below in Example 1, SD5AH4G-1D-1 exhibits cellobiohydrolase activity within a broad temperature range from 50 to 75° C., and across a broad pH range from 4.5 to 8. More specifically, the cellobiohydrolase activity of SD5AH4G-1D-1 increases with increasing temperature within a range from 50 to 75° C., but then tends to decrease rapidly above 75° C.

Further, in the presence of divalent metal ions, SD5AH4G-1D-1 exhibits high cellobiohydrolase activity at even higher temperatures than those observed in the absence of such metal ions. Actually, as shown below in Example 1, in the presence of calcium ions, SD5AH4G-1D-1 exhibits cellobiohydrolase activity within a broad temperature range from 50 to 85° C., and across a broad pH range from 4.5 to 8.

Generally, in a protein having some form of bioactivity, one or more amino acids can be deleted, substituted, or added, without impairing the bioactivity. In other words, in SD5AH4G-1D-1, one or more amino acids can be deleted, substituted, or added without impairing the cellobiohydrolase activity.

Hence, the thermostable cellobiohydrolase according to the present invention is a thermostable cellobiohydrolase having a cellobiohydrolase catalytic domain including any of the following (A) to (C):

(A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of PSA at least under conditions of 75° C. and pH 5.5, or (C) a polypeptide including an amino acid sequence having 75% or greater sequence identity with the amino acid sequence represented by SEQ ID NO: 1 or 2, and having hydrolysis activity against a substrate of PSA at least under conditions of 75° C. and pH 5.5.

The amino acid sequence represented by SEQ ID NO: 1 is the amino acid sequence encoded by the open reading frame SD5AH4G-1 (SEQ ID NO: 3) which was isolated from a compost culture sample using the method described below in Example 1, and which, based on database analysis, has a cellobiohydrolase sequence belonging to GH family 48.

In the above polypeptide of (B), the number of amino acids deleted, substituted, or added in the amino acid sequence represented by SEQ ID NO: 1 or 2 is preferably 1 to 20, more preferably 1 to 10, and still more preferably 1 to 5.

In the above polypeptide of (C), the sequence identity with the amino acid sequence represented by SEQ ID NO: 1 or 2 is not specifically limited as long as it is 75% or greater but less than 100%, but the sequence identity is preferably 80% or greater but less than 100%, more preferably 85% or greater but less than 100%, still more preferably 90% or greater but less than 100%, and most preferably 95% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity values between amino acid sequences in the present invention were obtained by calculation on the basis of an alignment obtained from the publicly known homology search software BLASTP.

The aforementioned polypeptides of (B) and (C) may be artificially designed, or may be homologs of SD5AH4G-1D-1 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1 or 2, by using a gene recombination technique to introduce amino acid mutation(s).

Each of the polypeptides of (A) to (C) has cellobiohydrolase activity at least under conditions of 75° C. and pH 5.5. As a result, a thermostable cellobiohydrolase can be obtained by having any of the polypeptides of (A) to (C) as the cellobiohydrolase catalytic domain.

The thermostable cellobiohydrolase according to the present invention uses at least PSA as a substrate. The thermostable cellobiohydrolase may also use other β-glucans or oligosaccharides besides PSA as a substrate. Examples of these other β-glucans or oligosaccharides include crystalline celluloses such as Avicel, bacterial microcrystalline cellulose (hereafter sometimes abbreviated as BMCC) and filter paper; carboxymethyl cellulose (CMC); glucans composed of β3-1,4 linkages; oligosaccharides composed of β-1,4 linkages such as cellobiose; xylan; p-nitrophenyl-β-D-galactopyranoside (hereafter sometimes abbreviated as PNP-GAL); p-nitrophenyl-β-D-xylopyranoside (hereafter often abbreviated as PNPX); glucans composed of β-1,3 and β-1,4 linkages such as lichenan; glucans composed of β-1,3 and β-1,6 linkages such as laminarin; glucans composed of β-1,3 linkages; glucans composed of β-1,6 linkages; and oligosaccharides composed of β-1,6 linkages such as gentiobiose.

The thermostable cellobiohydrolase according to the present invention preferably acts against Avicel and lichenan substrates in addition to PSA.

The thermostable cellobiohydrolase according to the present invention exhibits hydrolysis activity (cellobiohydrolase activity) against a PSA substrate, at least under conditions of pH 5.5, preferably within a temperature range from 65 to 75° C., more preferably within a temperature range from 60 to 75° C., and still more preferably within a temperature range from 50 to 75° C. The optimum temperature of the thermostable cellobiohydrolase according to the present invention is preferably within a range from 65 to 75° C., and more preferably within a range from 70 to 75° C.

The term "thermostable" used in relation to the thermostable cellobiohydrolase according to the present invention means the cellobiohydrolase has cellobiohydrolase activity within a temperature range from 50 to 75° C.

The optimum pH of the thermostable cellobiohydrolase according to the present invention is within a range from pH 5.0 to 6.0. The thermostable cellobiohydrolase according to the present invention preferably exhibits cellobiohydrolase activity at least within a range from pH 5.0 to 7.0, and more preferably exhibits cellobiohydrolase activity within a range from pH 4.5 to 8.0.

In the presence of divalent metal ions, the thermostable cellobiohydrolase according to the present invention preferably exhibits superior cellobiohydrolase activity at even higher temperatures than those observed in the absence of such metal ions, more preferably exhibits cellobiohydrolase activity at least under conditions of 80° C. and pH 5.5, and still more preferably exhibits cellobiohydrolase activity across a broad temperature range from 50 to 85° C., and across a broad pH range from 4.5 to 8.

In addition to cellobiohydrolase activity, the thermostable cellobiohydrolase according to the present invention may also have other cellulose hydrolysis activity besides the cellobiohydrolase activity. Examples of this other cellulose hydrolysis activity include xylanase activity, β-galactosidase activity, endoglucanase activity, xylosidase activity or β-glucosidase activity.

The thermostable cellobiohydrolase according to the present invention may be an enzyme composed solely of the cellobiohydrolase catalytic domain including any of the aforementioned polypeptides of (A) to (C), or may be an enzyme that also includes other domains. Examples of these other domains include other domains of conventionally known cellobiohydrolases besides the cellobiohydrolase catalytic domain. For example, the thermostable cellobiohydrolase according to the present invention also includes enzymes obtained by substituting the cellobiohydrolase catalytic domain in a publicly known cellobiohydrolase with any of the aforementioned polypeptides of (A) to (C).

When the thermostable cellobiohydrolase according to the present invention includes one or more other domains besides the cellobiohydrolase catalytic domain, the thermostable cellobiohydrolase preferably includes a cellulose-binding module (CBM). The cellulose-binding module may be positioned upstream (on the N-terminal side) or downstream (on the C-terminal side) of the cellobiohydrolase catalytic domain. Further, the cellulose-binding module and the cellobiohydrolase catalytic domain may be either bonded directly or bonded via a linker region of appropriate length. In the thermostable cellobiohydrolase according to the present invention, a cellulose-binding module preferably exists either upstream or downstream from the cellobiohydrolase catalytic domain with a linker region positioned therebetween, and a thermostable cellobiohydrolase in which a cellulose-binding module exists upstream of the cellobiohydrolase catalytic domain with a linker region positioned therebetween is particularly preferred.

The cellulose binding module included in the thermostable cellobiohydrolase according to the present invention is a region having the ability to bind cellulose, such as the ability to bind PSA or crystalline Avicel, and there are no particular limitations on the amino acid sequence of the module. Examples of the aforementioned cellulose-binding module include the types of cellulose-binding modules present in known proteins, and appropriately modified versions thereof. Further, in those cases where the thermostable cellobiohydrolase according to the present invention includes both the cellobiohydrolase catalytic domain and a cellulose-binding module, it is preferable that these are bonded via a linker sequence. There are no particular limitations on the amino acid sequence or the length and the like of the linker sequence.

The thermostable cellobiohydrolase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence.

Furthermore, the thermostable cellobiohydrolase according to the present invention may also have various types of tags added, for example at the N-terminal or the C-terminal, so as to facilitate easy purification in the case of generation using an expression system. Examples of tags that may be used include the types of tags widely used in the expression or purification of recombinant proteins, such as His tags, HA (hemagglutinin) tags, Myc tags and Flag tags.

In other words, one aspect of the thermostable cellobiohydrolase according to the present invention contains a cellobiohydrolase catalytic domain including any of the aforementioned polypeptides of (A) to (C); and also contains, according to need, at least one moiety selected from the group consisting of a cellulose-binding module positioned either upstream (on the N-terminal side) or downstream (on the C-terminal side) of the cellobiohydrolase catalytic domain, a linker region, a signal peptide added to either the N-terminal or the C-terminal of the thermostable cellobiohydrolase, and a tag added to either the N-terminal or the C-terminal of the thermostable cellobiohydrolase.

[Polynucleotide Encoding Thermostable Cellobiohydrolase]

The polynucleotide according to the present invention encodes the thermostable cellobiohydrolase according to the present invention. By introducing an expression vector incorporating the polynucleotide into a host, the thermostable cellobiohydrolase can be produced by using the expression system of the host.

Specifically, the polynucleotide according to the present invention is a polynucleotide having a region encoding a cellobiohydrolase catalytic domain, the region including any of the following nucleotide sequences (a) to (e):

(a) a nucleotide sequence encoding a polypeptide including the amino acid sequence represented by SEQ ID NO: 1 or 2, (b) a nucleotide sequence encoding a polypeptide which includes an amino acid sequence in which at least one amino acid has been deleted, substituted, or added in the amino acid sequence represented by SEQ ID NO: 1 or 2, and has hydrolysis activity against a substrate of PSA at least under conditions of 75° C. and pH 5.5, (c) a nucleotide sequence encoding a polypeptide which includes an amino acid sequence having 75% or greater sequence identity with the amino acid sequence represented by SEQ ID NO: 1 or 2, and has hydrolysis activity against a substrate of PSA at least under conditions of 75° C. and pH 5.5, (d) a nucleotide sequence having 75% or greater sequence identity with a nucleotide sequence represented by SEQ ID NO: 3 or 4, and encoding a polypeptide that has hydrolysis activity against a substrate of PSA at least under conditions of 75° C. and pH 5.5, or (e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of PSA at least under conditions of 75° C. and pH 5.5.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing that is performed after the incubation is preferably a 1×SSC solution containing 0.1% by mass of SDS, and is more preferably a 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 3, the nucleotide sequence represented by SEQ ID NO: 4, or a nucleotide sequence obtained by modifying the nucleotide sequence represented by SEQ ID NO: 3 or 4 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 3 or 4 may be chemically synthesized based on the nucleotide sequence information, or may be obtained from the natural world using gene recombination techniques as either a full length gene that encodes SD5AH4G-1D-1 (hereafter sometimes referred to as the "SD5AH4G-1D-1 gene" or the "gene clone SD5AH4G-1D-1") or a partial region thereof including the cellobiohydrolase catalytic domain. The full length of the SD5AH4G-1D-1 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 3 or 4. The cDNA synthesized by a reverse transcription reaction using mRNA recovered from the sample as a template may also be used as a template.

In the aforementioned nucleotide sequence of (d), the sequence identity with the nucleotide sequence represented by SEQ ID NO: 3 or 4 is not specifically limited as long as it is 75% or greater but less than 100%, but the sequence identity is preferably 80% or greater but less than 100%, more preferably 85% or greater but less than 100%, still more preferably 90% or greater but less than 100%, and most preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity values between nucleotide sequences in the present invention were obtained by calculation on the basis of an alignment obtained from the publicly known homology search software BLASTN.

For example, each of the polynucleotides including an aforementioned nucleotide sequence of (b), (c) or (d) can be artificially synthesized by deleting, substituting, or adding one or a plurality of nucleotides in a polynucleotide including the nucleotide sequence represented by SEQ ID NO: 3 or 4. Further, the nucleotide sequence of (b), (c) or (d) may also be a full length sequence of a homologous gene of the SD5AH4G-1D-1 gene or a partial sequence thereof. The homologous gene of the SD5AH4G-1D-1 gene can be obtained by a gene recombination technique used in obtaining homologous genes of a gene for which the nucleotide sequence is already known.

The polynucleotide according to the present invention may have only the region encoding the cellobiohydrolase catalytic domain, or may also have, in addition to this region, one or more other regions encoding a cellulose-binding module, a linker sequence, various types of signal peptides, or various types of tags or the like. In other words, one aspect of the polynucleotide according to the present invention contains a region encoding the cellobiohydrolase catalytic domain, the region including one of the aforementioned nucleotide sequences of (a) to (e), and also contains, according to need, a region encoding at least one moiety selected from the group consisting of a cellulose-binding module, a linker region, a signal peptide and a tag.

[Expression Vector]

The expression vector according to the present invention incorporates the aforementioned polynucleotide according to the present invention, and is capable of expressing, in a host cell, a polypeptide having cellobiohydrolase activity at least under conditions of 75° C. and pH 5.5. In other words, the expression vector of the present invention is an expression vector into which the polynucleotide according to the present invention has been incorporated in a state capable of expressing the thermostable cellobiohydrolase according to the present invention. More specifically, an expression cassette composed, in order from the upstream side, of DNA having a promoter sequence, the aforementioned polynucleotide according to the present invention and DNA having a terminator sequence, must be incorporated into the expression vector. Incorporation of the polynucleotide into the expression vector can be achieved using known gene recombination techniques, or a commercially available expression vector preparation kit may be used.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as E. coli, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of cells transformed by the expression vector and non-transformed cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the thermostable cellobiohydrolase according to the present invention can be expressed. Conventionally known cellobiohydrolases tend to have a narrow range of expression hosts, meaning heterologous expression is often difficult. However, the thermostable cellobiohydrolase according to the present invention can be expressed in a wide range of expression hosts, including *E. coli*, yeasts, filamentous fungi and higher plant chloroplasts. Accordingly, the host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced.

By culturing a transformant of *E. coli*, the thermostable cellobiohydrolase according to the present invention can be generated more easily and in large amounts. On the other hand, because proteins are glycosylated in eukaryotic cells, by using a transformant of a eukaryotic cell, a thermostable cellobiohydrolase can be generated which exhibits superior thermal stability to that achieved by using a transformant of a prokaryotic cell.

There are no particular limitations on the method used for producing the transformant using the expression vector, and the types of methods typically used in the production of transformants can be employed. Examples of methods that can be used include an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable Cellobiohydrolase]

The method for producing a thermostable cellobiohydrolase according to the present invention is a method for generating a thermostable cellobiohydrolase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable cellobiohydrolase according to the present invention can be expressed constitutively within the transformant. On the other hand, in the case of a transformant produced using a so-called expression inducible promoter to induce the expression by means of a specific compound or temperature condition or the like, the thermostable cellobiohydrolase according to the present invention can be expressed in the transformant by conducting an induction treatment suitable for the respective expression-inducing condition.

The thermostable cellobiohydrolase generated by the transformant may be used in a state where it is retained inside the transformant, or may be extracted from the transformant and purified.

The method used for extracting and purifying the thermostable cellobiohydrolase from the transformant is not particularly limited, as long as the method does not impair the activity of the thermostable cellobiohydrolase, and extraction can be carried out by methods commonly used for extracting polypeptides from cells or biological tissue. Examples of the method include a method in which the transformant is immersed in an appropriate extraction buffer to extract the thermostable cellobiohydrolase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable cellobiohydrolase in the liquid extract can be purified by known purification methods such as a salting-out method, ultrafiltration method, or chromatography method.

If the thermostable cellobiohydrolase according to the present invention is expressed in the transformant in a state having a secretory signal peptide, then a solution containing the thermostable cellobiohydrolase can be readily obtained by culturing the transformant and then collecting the culture liquid supernatant obtained by removal of the transformant from the obtained culture. Further, if the thermostable cellobiohydrolase according to the present invention has a tag such as an His tag, then the thermostable cellobiohydrolase in the liquid extract or in the culture supernatant can be easily purified by an affinity chromatography method using the tag.

In other words, the method for producing a thermostable cellobiohydrolase according to the present invention includes generating the thermostable cellobiohydrolase within the transformant according to the present invention, and also includes, according to need, extracting the thermostable cellobiohydrolase from the transformant and purifying the thermostable cellobiohydrolase.

[Glycoside Hydrolase Mixture]

The glycoside hydrolase mixture according to the present invention includes the aforementioned thermostable cellobiohydrolase according to the present invention or a thermostable cellobiohydrolase produced by the method for producing a thermostable cellobiohydrolase according to the present invention, and at least one other glycoside hydrolase. The thermostable cellobiohydrolase produced by the aforementioned method for producing a thermostable cellobiohydrolase according to the present invention may be in a state where it is incorporated inside the transformant, or may be extracted from the transformant and purified. By using the thermostable cellobiohydrolase according to the present invention as a mixture with one or more other glycoside hydrolases in a cellulose hydrolysis reaction, materials composed of lignocellulose containing persistent cellulose can be degraded more efficiently.

There are no particular limitations on the other glycoside hydrolase besides the aforementioned thermostable cellobiohydrolase included in the glycoside hydrolase mixture, as long as it exhibits cellulose hydrolysis activity. Examples of the other glycoside hydrolase besides the aforementioned thermostable cellobiohydrolase included in the glycoside hydrolase mixture include hemicellulases such as xylanases and β-xylosidases, as well as cellobiohydrolases, β-glucosidases and endoglucanases. The glycoside hydrolase mixture according to the present invention is preferably a mixture containing at least one glycoside hydrolase selected from among hemicellulases and endoglucanases in addition to the aforementioned thermostable cellobiohydrolase, and is more preferably a mixture containing both a hemicellulase and an endoglucanase in addition to the aforementioned thermostable cellobiohydrolase. Among the various possibilities, the glycoside hydrolase mixture according to the present invention is preferably a mixture containing at least one glycoside hydrolase selected from the group consisting of xylanases, β-xylosidases and endoglucanases in addition to the aforementioned thermostable cellobiohydrolase, and is more preferably a mixture containing all of a xylanase, a β-xylosidase and an endoglucanase in addition to the thermostable cellobiohydrolase.

It is particularly preferable that the glycoside hydrolase mixture contains at least both the aforementioned thermostable cellobiohydrolase and a cellobiohydrolase of the GH6 family.

The reason for this preference is that by using a combination of the aforementioned thermostable cellobiohydrolase and a cellobiohydrolase of the GH6 family, a level of cellobiohydrolase activity can be obtained that is superior to that observed when either of the cellobiohydrolases is used alone.

The other glycoside hydrolase included in the glycoside hydrolase mixture is preferably a thermostable glycoside hydrolase having glycoside hydrolase activity at least at 75° C., and is more preferably a thermostable glycoside hydrolase having glycoside hydrolase activity at 70 to 80° C. By ensuring that all of the enzymes contained in the glycoside hydrolase mixture are thermostable (that is, have an optimum temperature for the enzymatic activity or a thermal denaturation temperature (melting temperature) for the enzyme protein of 70° C. or higher), the cellulose degradation reaction by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material containing cellulose, such as a material composed of lignocellulose containing cellulose, it becomes possible to conduct a hydrolysis reaction of the material in a high-temperature environment in which the hydrolysis temperature is from 70 to 80° C. (namely, a high-temperature hydrolysis). With this high-temperature hydrolysis, the amount of enzymes used and the time required for the hydrolysis can be reduced markedly, and the hydrolysis costs can be cut dramatically.

[Method for Producing Cellulose Degradation Product]

The method for producing a cellulose degradation product according to the present invention is a method for obtaining a cellulose degradation product by hydrolyzing a material containing cellulose with the thermostable cellobiohydrolase according to the present invention. More specifically, the method of the present invention is a method for producing a cellulose material degradation product (for example, a degradation product containing cellobiose and glucose and the like) by bringing a material containing cellulose into contact with the thermostable cellobiohydrolase according to the present invention, the transformant according to the present invention, a thermostable cellobiohydrolase produced using the method for producing a thermostable cellobiohydrolase according to the present invention, or the glycoside hydrolase mixture according to the present invention.

There are no particular limitations on the material containing cellulose, provided the material contains cellulose. Specific examples of the material include cellulosic biomass such as weeds and agricultural waste materials, or used paper or the like. The material containing cellulose is preferably subjected to a mechanical treatment such as crushing or shredding, a chemical treatment with acid or alkali or the like, or a treatment such as immersion or dissolution in an appropriate buffer, prior to being brought into contact with the thermostable cellobiohydrolase according to the present invention.

The reaction conditions for the hydrolysis reaction of the above material by the thermostable cellobiohydrolase according to the present invention may be any conditions under which the thermostable cellobiohydrolase exhibits cellobiohydrolase activity. For example, in the absence of divalent metal ions, the reaction is preferably conducted at a temperature of 50 to 75° C. and a pH of 4.5 to 8.0, and is more preferably conducted at a temperature of 65 to 75° C. and a pH of 5.0 to 6.0. Further, in the presence of divalent metal ions, the reaction is preferably conducted at a temperature of 50 to 85° C. and a pH of 4.5 to 8.0, and is more preferably conducted at a temperature of 70 to 85° C. and a pH of 5.0 to 6.0. The reaction time for the hydrolysis reaction may be adjusted appropriately with due consideration of the type, the method of pretreatment, and the amount and the like of the cellulose material supplied to the hydrolysis reaction. For example, the hydrolysis reaction may be performed for a reaction time of 10 minutes to 100 hours, but in the case of degradation of a cellulosic biomass, the hydrolysis reaction is typically performed for a reaction time of 1 hour to 100 hours.

In the hydrolysis reaction of the material containing cellulose, it is also preferable to use at least one other type of glycoside hydrolase in addition to the thermostable cellobiohydrolase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 75° C., and preferably at least at temperatures of 70 to 80° C. Further, one aspect of the aforementioned method for producing a cellulose degradation product uses the thermostable cellobiohydrolase according to the present invention, the transformant according to the present invention, or a thermostable cellobiohydrolase produced by the method for producing a thermostable cellobiohydrolase according to the present invention, whereas another aspect of the method uses the aforementioned glycoside hydrolase mixture.

EXAMPLES

Next, the present invention is described in further detail based on a series of examples, but the present invention is in no way limited by the following examples.

Example 1

Cloning of Novel Thermostable Cellobiohydrolase from Compost Culture Sample

<1> DNA Extraction from Compost Culture Sample and Whole Genome Sequencing (WGS)

With the purpose of searching for genes of thermostable cellobiohydrolases (having an optimum temperature of 55°

C. or higher), nucleotide sequencing was conducted of the genomic DNA of the microbial flora contained in compost culture samples.

Each of the compost culture samples was prepared in the following manner. First, the compost was collected. The temperature of the compost upon collection was within a range from 20 to 68° C. Next, about 0.5 g of the collected compost, two 1.5 cm square sheets of a thick paper (about 250 mg, gel-blotting paper GB005, manufactured by Whatman plc) as a carbon source, and one dialysis tube having dimensions of 1.2 cm×1.5 cm made of regenerated cellulose (Spectra/Por 7 RC dialysis tube, manufactured by Spectrum Laboratories, Inc.) were added to 20 mL of a modified AGS liquid medium detailed in Table 1, and a rotary shaking culture was performed at 65° C. and 120 rpm using a 125 mL conical flask fitted with baffles. After culturing for one week, and following confirmation of the disappearance of the carbon source from inside the conical flask and the proliferation of bacteria, 0.5 mL of the culture medium was subcultured in a fresh 20 mL sample of the modified AGS liquid medium, and a carbon source was then added and culturing was performed in the same manner as described above.

After three repetitions of this subculturing process, the bacterial cells were collected by a centrifuging (5,000 rpm, 10 minutes, 4° C.).

TABLE 1

| Modified AGS medium components | (/L) |
|---|---|
| L-arginine | 1 g |
| $K_2HPO_4$ | 1 g |
| NaCl | 1 g |
| $MgSO_4 \cdot 7H_2O$ | 0.5 g |
| $Fe_2(SO_4)_3 \cdot 6H_2O$ | 10 mg |
| $CuSO_4 \cdot 5H_2O$ | 1 mg |
| $ZnSO_4 \cdot 7H_2O$ | 1 mg |
| $MnSO_4 \cdot 4H_2O$ | 1 mg |

DNA was extracted from the collected bacterial cells using a DNA extraction kit (ISOIL for Beads Beating, manufactured by Nippon Gene Co., Ltd.). One μg of the extracted DNA was subjected to shotgun sequencing of the genomic DNA using a GS FLX+ 454 manufactured by Roche Diagnostics Ltd.

Genomic DNA sequencing of the compost culture sample SD5AH4G yielded a whole genome sequence (WGS) data set having an average read length of 532 bp, a total read number of 2,471,267, and a total quantity of sequenced genomes of 1.324 Gbp.

<2> Assembly and Statistics of Compost Culture Sample Genomic Data

The output from the Roche 454 (sff file) was subjected to a second base calling using PyroBayes (Quinlan et al., Nature Methods, 2008, vol. 5, pp. 179 to 181), and a FASTA format sequence file and Quality value file were obtained. Ends were cut from the obtained sequence reads to improve quality, and the reads were assembled using the 454 Life Sciences assembly software Newbler version 2.5.3. Assembly was performed under settings including "minimum acceptable overlap match (mi)=0.9", "option: —large (for large or complex genomes, speeds up assembly but reduces accuracy)".

The total contig length of all contigs assembled to at least 100 bp totaled 38,078,551 bp, and this data set was used for cellulase gene analysis. Of the total read number of 4,942,524 reads, 2,858,018 reads were assembled into contigs having an average of at least 2,617 bp (a total of 14,551 contigs), of which the maximum contig length was 114,826 bp.

<3> Prediction of Open Reading Frames (ORFs) of Cellobiohydrolase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: 2011/12/9) from the UniProt database, and a proteome local database of these glycoside hydrolase genes was constructed. The annotation software MetaGeneAnnotator (Noguchi et al., MetaGeneAnnotator: Detecting Species-Specific Patterns of Ribosomal Binding Site for Precise Gene Prediction in Anonymous Prokaryotic and Phage Genomes, DNA Res., 2008, 15, pp. 387 to 396) was used to predict gene regions (=open reading frames) from the contig sequences obtained in the above section <2>. In order to extract glycoside hydrolase genes from the predicted ORFs, reference was made to the local database using BLASTP (blastall ver. 2.2.18). Furthermore, the option conditions for BLASTP were set such that: "Filter query sequence=false", "Expectation value (E)<$1e^{-20}$" (hereafter, default values were set such that: "Cost to open a gap=−1", "Cost to extended gap=−1", "X dropoff value for gapped alignment=0", "Threshold for extending hits=0", and "Word size=default"), and the hit sequences were collected as glycoside hydrolase genes.

<4> Glycoside Hydrolase (GH) Family Classification of Genes

Functional classification of the sequences collected in section <3> above, including various glycoside hydrolases such as cellulases, endohemicellulases and debranching enzymes, was performed with reference to the protein functional domain sequence database Pfam HMMs (Pfam version 23.0 and HMMER v2.3; Finn et al., Nucleic Acids Research Database, 2010, Issue 38, pp. D211 to 222). Specifically, the glycoside hydrolase (GH) family of each sequence was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff <$1e^{-5}$; Database=Pfam_fs (models that can be used to find fragments of the represented domains in a sequence)).

The GH family classification results of the 10 ORFs predicted as cellobiohydrolase candidate sequences (4 full-length ORFs and 6 partial length ORFs) are shown in Table 2. ORFs for which the coverage of the GH catalytic domain sequence was 70% or greater were counted. As shown in Table 2, from the genome SD5AH4G, two full-length ORFs belonging to the GH family 6, one full-length ORF belonging to the GH family 26, and one full-length ORF belonging to the GH family 48 were obtained. Primers were designed for all of these ORFs, and the genes were cloned from the compost culture sample-derived DNA by PCR. As a result, the cellobiohydrolase gene SD5AH4G-1D-1 was isolated from the open reading frame SD5AH4G-1 belonging to the GH family 48 and encoding an amino acid sequence having a cellobiohydrolase sequence.

TABLE 2

|  | GH6 | GH9 | GH26 | GH48 | Total |
|---|---|---|---|---|---|
| Full-length ORFs | 2 | 0 | 1 | 1 | 4 |
| Partial length ORFs | 1 | 3 | 0 | 2 | 6 |
| Total | 3 | 3 | 1 | 3 | 10 |

<5> Open Reading Frame SD5AH4G-1

The open reading frame SD5AH4G-1 (SEQ ID NO: 3) encoded a polypeptide (SEQ ID NO: 1) composed of 1,146 amino acid residues, and this polypeptide was a full-length sequence in which the amino acid residue at position 1 started from a methionine (M), and the 3'-end ended with a termination codon. Based on the sequence homology of the motif, it was predicted that the 41 amino acid residues from the methionine at position 1 through to the alanine (A) at position 41 encoded by the open reading frame SD5AH4G-1 represented a secretory signal (SignalP 4.1), that the 688 amino acid residues from the arginine (R) at position 51 through to the leucine (L) at position 738 represented the catalytic domain of the glycoside hydrolase family 48, and that the 81 amino acid residues from the glutamic acid (E) at position 817 through to the leucine at position 897 and the 81 amino acid residues from the glutamine (Q) at position 1,001 through to the isoleucine (I) at position 1,081 represented CBM3 domains. The amino acid sequence encoded by the ORF exhibited 73% amino acid sequence identity with the cellulose 1,4-β-cellobiosidase of the Firmicutes bacterium *Paenibacillus mucilaginosus* (Genbank registration ID: AFK65316.1) (SEQ ID NO: 9) in the GH48 catalytic domain.

The sequence homology values were calculated using the ClustalW algorithm.

<6> Cellobiohydrolase Gene SD5AH4G-1D-1

The cellobiohydrolase gene SD5AH4G-1D-1 is a portion of the amino acid sequence encoded by the open reading frame SD5AH4G-1 that includes the GH family 48 catalytic domain from the aspartic acid (D) at position 44 through to the proline (P) at position 745. The amino acid sequence of the cellobiohydrolase gene SD5AH4G-1D-1 (hereafter also referred to as the amino acid sequence of the cellobiohydrolase gene clone SD5AH4G-1D-1) (SEQ ID NO: 2) was identical with the corresponding region of the amino acid sequence encoded by the open reading frame SD5AH4G-1, and the nucleotide sequence (SEQ ID NO: 4) encoding the amino acid sequence of the cellobiohydrolase gene SD5AH4G-1D-1 was identical with the corresponding region of the open reading frame SD5AH4G-1.

Figure 1:
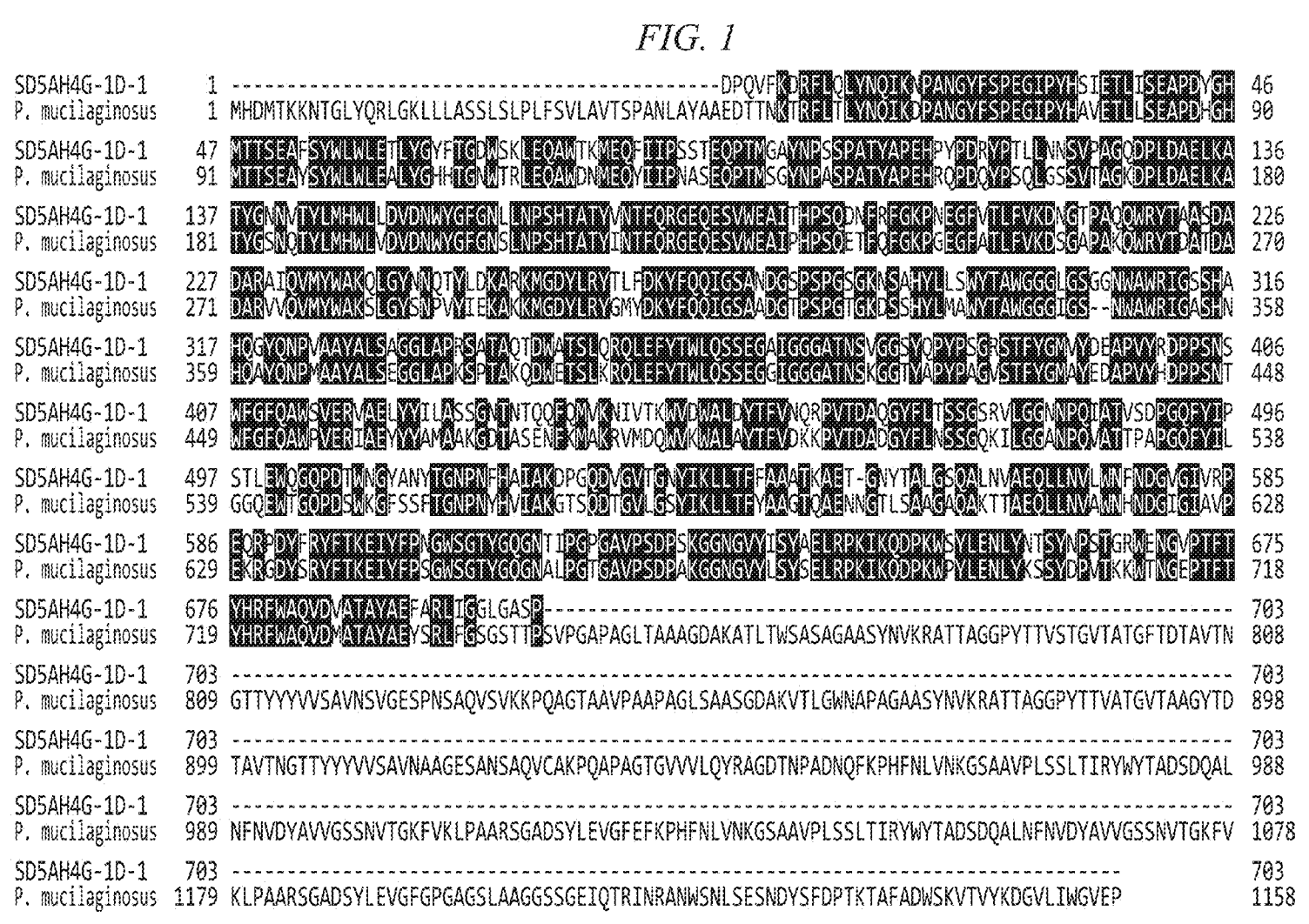

FIG. 1 shows the alignment of the amino acid sequence (SEQ ID NO: 2) of the cellobiohydrolase gene clone SD5AH4G-1D-1 and the amino acid sequence (SEQ ID NO: 9) of the cellulose 1,4-β-cellobiosidase of *Paenibacillus mucilaginosus*. In FIG. 1, the amino acids shown in white on black are the amino acid residues identical to both amino acid sequences, and "-" indicates a gap in a sequence.

<7> Expression and Purification of Cellobiohydrolase Protein

Using a forward primer including a nucleotide sequence represented by SEQ ID NO: 7 (5'-GTGATGGACCCGCAGGTTTTCAAG-3': wherein 6 nucleotides (GTGATG) were added to the 5'-end of the nucleotide sequence represented by SEQ ID NO: 5, and the 5'-end was phosphorylated), and a reverse primer including a nucleotide sequence represented by SEQ ID NO: 8 (5'-GTAAGCTTACGGCGAAGCGCCCAAAC-3': wherein a termination codon and a recognition sequence for the restriction enzyme Hind III were added to the 5'-end of the nucleotide sequence represented by SEQ ID NO: 6, the Hind III being a sequence used for vector insertion), a PCR product that had been amplified by KOD-Plus-Neo (manufactured by Toyobo Co., Ltd.) was inserted into a pLEAD5 vector (manufactured by Nippon Gene Co., Ltd.) and transformed into an *E. coli* JM109 strain using the SD5AH4G-1D-1 gene that had been isolated by PCR cloning as a template. The nucleotide sequence represented by SEQ ID NO: 5 is homologous (identical) with the partial sequence composed of the nucleotides from positions 130 to 147 of the nucleotide sequence represented by SEQ ID NO: 3. Further, the nucleotide sequence represented by SEQ ID NO: 6 is complementary with the partial sequence composed of the nucleotides from positions 2,222 to 2,238 of the nucleotide sequence represented by SEQ ID NO: 3. Positive clones were selected by colony PCR and cultured in an LB liquid medium containing 50 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation).

The transformed *E. coli* clone having the SD5AH4G-1D-1/pLEAD5 plasmid for which the sequence had been confirmed was inoculated into a Turbo Broth medium (manufactured by Athena Environmental Sciences, Inc.) containing 50 mg/L of ampicillin, and was cultured for about 20 hours to express the target protein. Following culturing, the *E. coli* was collected by centrifugation, and an amount of 50 mM Tris-HCl buffer (pH 8.0) equivalent to 1/10 of the volume of the culture liquid was added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant *E. coli* containing the target protein. This gene recombinant *E. coli* crude extract was filtered through a filter (pore size φ=0.45 μm, manufactured by EMD Millipore Corporation), and the resulting filtrate was used as a gene recombinant *E. coli* homogeneous supernatant.

The gene recombinant *E. coli* homogeneous supernatant was loaded onto an ion exchange column HiTrap Q HP (manufactured by GE Healthcare, Inc.) equilibrated with a 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in a 50 mM Tris-HCl buffer (pH 8.0) containing 1 M of NaCl. The fractions exhibiting cellobiohydrolase activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with cellobiohydrolase activity following the buffer exchange were loaded onto a hydrophobic interaction separation column HiTrap Phenyl HP (manufactured by GE Healthcare, Inc.) equilibrated with the same buffer solution, and the proteins were fractionated with a concentration gradient of 0 to 100% in a 50 mM Tris-HCl buffer (pH 8.0). The fractions exhibiting cellobiohydrolase activity were pooled and then concentrated using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with a 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting cellobiohydrolase activity were pooled, a buffer exchange to a 50 mM Tris-HCl buffer (pH 8.0) and subsequent concentration were performed, and the proteins were fractionated in the same manner as that described above using the HiTrap Q HP. The fractions exhibiting cellobiohydrolase activity were pooled, and a buffer exchange to a 50 mM Tris-HCl buffer (pH 8.0) and subsequent concentration were performed, yielding a purified enzyme with a final concentration of about 1 mg/mL.

The gene recombinant E. coli homogenous supernatant and the purified enzyme (purified cellobiohydrolase protein) were checked by SDS-PAGE (SDS-polyacrylamide gel electrophoresis) analysis. The SDS-PAGE of the gene recombinant E. coli homogenous supernatant and the purified enzyme was performed using a Mini-PROTEAN TGX Stain-Free gel (manufactured by Bio-Rad Laboratories, Inc.). The supernatant and the purified enzyme were each mixed with Tris-SDS βME treatment solution (manufactured by Cosmo Bio Co. Ltd.) at 1:1, and following treatment of the thus obtained electrophoresis samples at 100° C. for 10 minutes, 10 μL of the gene recombinant E. coli homogenous supernatant and 2 μg of the purified enzyme respectively were subjected to electrophoresis. Following completion of the electrophoresis, the protein bands were visualized and detected by CBB staining.

FIG. 2 shows the SDS-PAGE analysis results of the gene recombinant E. coli homogenous supernatant prepared from the transformed E. coli into which the SD5AH4G-1D-1 gene had been introduced, and the purified enzyme produced from the gene recombinant E. coli homogenous supernatant. The figure shows an electrophoretic pattern in which lane 1 represents a protein mass marker, lane 2 represents the gene recombinant E. coli homogenous supernatant, and lane 3 represents the purified enzyme. The results revealed a strong band in the gene recombinant E. coli homogenous supernatant (lane 2) near the mass of 78.6 kDa expected from the amino acid sequence (SEQ ID NO: 2), and a single band corresponding with this band (indicated by an arrow in the figure) was observed in the purified enzyme (lane 3).

<8> Cellobiohydrolase Activity Against PSA Substrate

The cellobiohydrolase activity of the enzyme protein (SD5AH4G-1D-1) encoded by the SD5AH4G-1D-1 gene against a substrate of PSA was investigated. In the measurements, a solution prepared by diluting the purified enzyme obtained in section <7> above with a 0.05 M Tris-HCl buffer (pH 8.0) to obtain a concentration of 1 mg/mL was used.

The PSA used as the substrate was prepared by first dissolving an Avicel powder (microcrystalline cellulose powder, manufactured by Merck & Co., Inc.) in a phosphoric acid solution, subsequently adding purified water to cause precipitation, and then washing until a pH of 5 or greater was obtained. The PSA used in the experiments described below was all prepared by this method.

A sample tube with a volume of 1.5 mL was used as the reaction vessel, and the reaction solution was composed of 10 μL of the diluted purified enzyme, 40 μL of purified water, 50 μL of a 200 mM acetate buffer (pH 5.5), and 100 μL of a 1% by mass PSA solution. In all measurements, a mixed solution prepared by replacing the purified enzyme solution with a 50 mM Tris-HCl buffer (pH 8.0) and then reacting the solution under the same conditions was used as a control. Further, the substrate solution and a mixed solution of the purified enzyme solution, the purified water and the buffer were held separately at the reaction temperature for five minutes (pre-incubation) before being mixed to initiate the reaction. During reaction, all of the mixed solutions were adjusted to the prescribed temperature using a Thermomixer (manufactured by Eppendorf AG). Following completion of the 20-minute reaction, 3,5-dinitrosalicylic acid reagent (DNS solution) was added to each mixed solution in a volume equal to that of the solution, and the resulting mixture was heated at 100° C. for 5 minutes, cooled down on ice for 5 minutes, and then centrifuged at 17,500 g for 5 minutes at room temperature to obtain a supernatant. The amount of reducing sugars within the supernatant was determined by measuring the absorbance at 540 nm using a spectrophotometer, calculating the amount of reducing sugars using a calibration curve prepared with glucose, and then calculating the amount of reducing sugars produced by the enzymatic hydrolysis based on the difference from the control. The enzymatic activity for producing 1 μmol of reducing sugars per minute was defined as 1 U, and the value obtained by dividing this activity by the amount of protein was defined as the specific activity (U/mg). Each measurement was performed for three independent experiments, and a mean value and the standard errors were determined.

<9> Substrate Specificity of SD5AH4G-1D-1

The hydrolysis activity of the enzyme protein SD5AH4G-1D-1 against various cellulose substrates and hemicellulose substrates was investigated. In the measurements, a solution prepared by diluting the purified enzyme obtained in section <7> above with a 0.05 M Tris-HCl buffer (pH 8.0) to obtain a concentration of 1 mg/mL was used. For the substrates, PSA, Avicel powder, CMC (manufactured by Sigma-Aldrich Co. LLC.), xylan (derived from beech wood, manufactured by Sigma-Aldrich Co. LLC.), lichenan (manufactured by MP Biomedicals, LLC), laminarin (derived from Laminaria digitata, manufactured by Sigma-Aldrich Co. LLC.), PNPC (p-nitrophenyl-3-D-cellobioside, manufactured by Sigma-Aldrich Co. LLC.) and PNPG (p-nitrophenyl-β-D-glucopyranoside, manufactured by Sigma-Aldrich Co. LLC.) were used.

Specifically, when PSA, Avicel powder, CMC, xylan, lichenan or laminarin was used as the substrate, with the exceptions of using a 1% by mass aqueous solution as the substrate solution and performing the reaction at 70° C., reaction was performed in the same manner as that described above in section <8>, the amount of reducing sugars produced by the enzymatic hydrolysis was determined, and the specific activity (U/mg) was calculated. For the xylan measurement, a calibration curve prepared using xylose was used. In addition, in the case of the Avicel, the hydrolysis activity in the reaction time of 2 hours was investigated.

When PNPC or PNPG was used as the substrate, with the exceptions of using a 10 mM aqueous solution as the substrate solution and performing the reaction at 70° C., reaction was first performed in the same manner as that described above in section <8>, and following the 20-minute reaction, an equal volume of a 200 mM aqueous solution of sodium carbonate was added, and the resulting mixture was then centrifuged for 5 minutes to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis on the basis of the difference from the control. The enzymatic activity for producing 1 μmol of p-nitrophenol per minute was defined as 1 U, and the value obtained by dividing this activity by the amount of protein was defined as the specific activity (U/mg).

Figure 3:
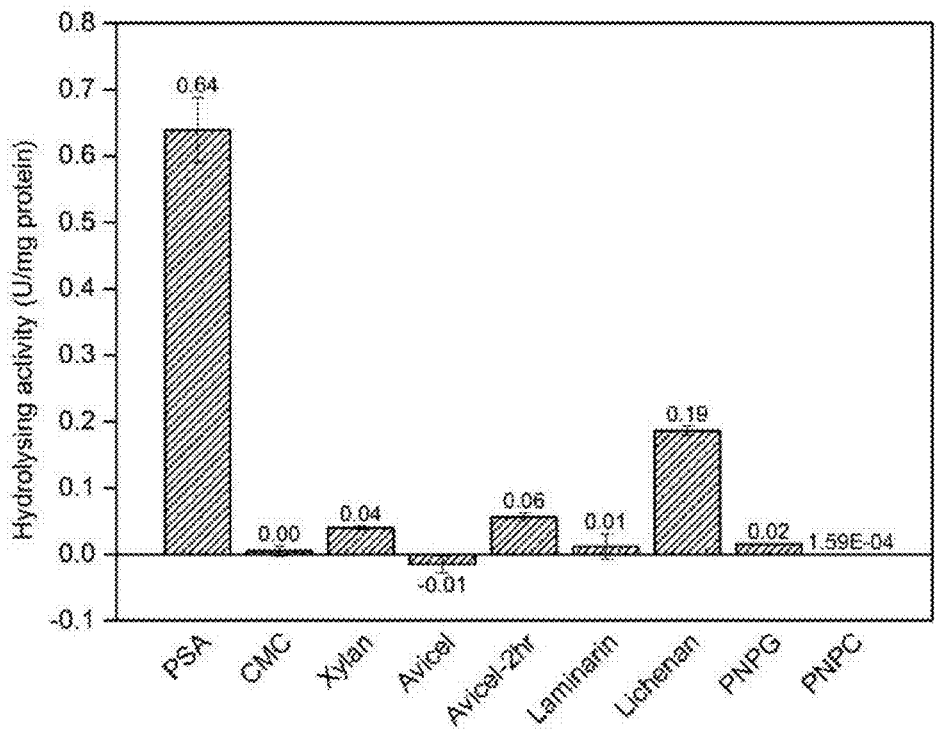
FIG. 3 is a diagram showing the results of measuring the hydrolysis activity against various substrates of the SD5AH4G-1D-1 protein obtained by expressing the SD5AH4G-1D-1 gene in *E. coli* in Example 1.

The measurement results are shown in FIG. 3. The results revealed that SD5AH4G-1D-1 exhibited hydrolysis activity against PSA, and also exhibited weak hydrolysis activity against Avicel (two-hour reaction) and lichenan, but exhibited almost no hydrolysis activity against CMC, laminarin, xylan, PNPG and PNPC.

<10> Temperature and pH Dependencies of Cellobiohydrolase of SD5AH4G-1D-1

The temperature dependency of the PSA hydrolysis activity of SD5AH4G-1D-1 was investigated. Specifically, with the exception of setting the reaction temperature to 40, 50, 60, 65, 70, 75, 80, 85 or 90° C., reaction was performed in the same manner as that described above in section <8>, and for each temperature, the amount of reducing sugars produced by the enzymatic hydrolysis was determined and the PSA hydrolysis activity (U/mg) was calculated.

Further, measurements were also performed using reaction solutions in which a 10 mM aqueous solution of $CaCl_2$ was added instead of the 40 μL of purified water, and for each temperature, the amount of reducing sugars produced by the enzymatic hydrolysis was determined and the PSA hydrolysis activity (U/mg) was calculated.

Figure 4:
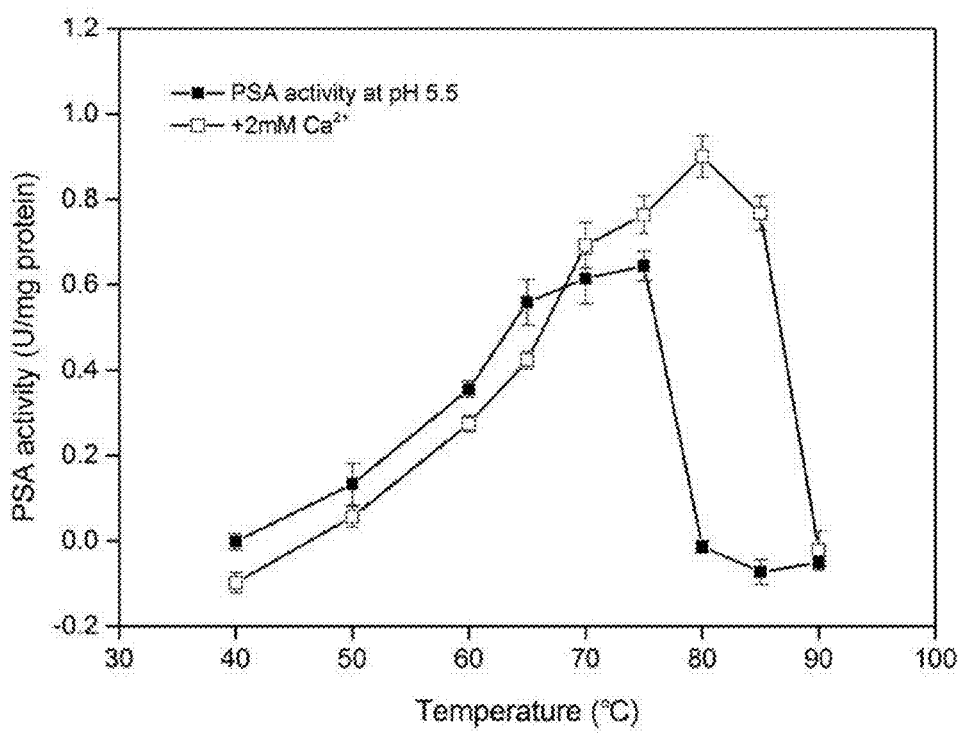
FIG. 4 is a diagram showing the results of measuring the PSA hydrolysis activity (pH 5.5) at various temperatures, either in the presence of calcium ions or in the absence of calcium ions, of the SD5AH4G-1D-1 protein obtained by expressing the SD5AH4G-1D-1 gene in *E. coli* in Example 1.

The results are shown in FIG. 4. In the absence of calcium ions (labeled as "PSA activity at pH 5.5" in the figure), SD5AH4G-1D-1 exhibited PSA hydrolysis activity in a temperature range from 50 to 75° C. Further, in the presence of calcium ions (labeled as "+2 mM $Ca^{2+}$" in the figure), SD5AH4G-1D-1 exhibited PSA hydrolysis activity in a temperature range from 50 to 85° C. The optimum temperature ($T_{opt}$) at which the highest activity was observed was 75° C. in the absence of calcium ions and 80° C. in the presence of calcium ions.

The pH dependency of the PSA hydrolysis activity of SD5AH4G-1D-1 was also investigated. Specifically, with the exception of performing the reaction at 70° C. using 50 μL of either a 200 mM acetate buffer (pH 4 to 6) or a 200 mM phosphate buffer (pH 6 to 8), reaction was performed in the same manner as that described above in section <8>, and for each pH value, the amount of reducing sugars produced by the enzymatic hydrolysis was determined and the PSA hydrolysis activity (U/mg) was calculated.

Figure 5:
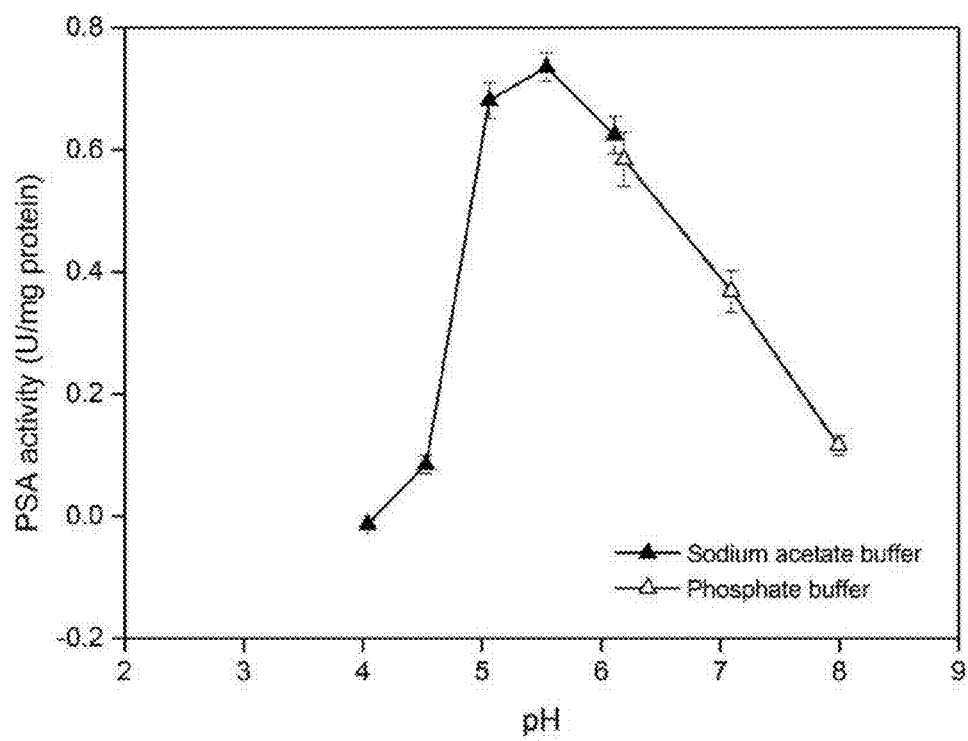
FIG. 5 is a diagram showing the results of measuring the PSA hydrolysis activity (70° C.) at various pH values of the SD5AH4G-1D-1 protein obtained by expressing the SD5AH4G-1D-1 gene in *E. coli* in Example 1.

The results are shown in FIG. 5. For the pH values, the actual measurement value obtained for the mixed solution containing the substrate, the buffer and the enzyme was plotted. SD5AH4G-1D-1 exhibited PSA hydrolysis activity in a pH range from pH 4.5 to 8. The optimum pH was 5.54 (actual measurement value for the mixed solution containing the substrate, the buffer and the enzyme).

<11> Cellobiohydrolase Activity of SD5AH4G-1D-1 when Mixed with GH6 Cellobiohydrolase The cellulose hydrolysis activity of a mixture of SD5AH4G-1D-1 and a GH6 cellobiohydrolase was investigated. Using AR19G-166-RA (SEQ ID NO: 10) as the GH6 cellobiohydrolase, the mixing ratio (mass ratio) with the SD5AH4G-1D-1 was changed within a range from 10:0 to 0:10 without altering the total amount of enzyme, and the hydrolysis activity was measured against PSA and Avicel. Specifically, reaction solutions composed of 10 μL of a mixed solution of the purified enzymes, 40 μL of a 10 mM $CaCl_2$ solution, 50 μL of a 200 mM acetate buffer (pH 5.5), and 100 μL of a 1% by mass aqueous solution of PSA or Avicel were reacted, either at 80° C. for 20 minutes in the case of the PSA substrate, or at 80° C. for 2 hours in the case of the Avicel substrate. Following reaction, the amount of reducing sugars produced by the enzymatic hydrolysis was determined, and the specific activity (U/mg) was calculated in the same manner as that described above in section <8>. The enzymatic activity was recorded as a relative activity value (%), relative to a value of 100% for the case where the mixing ratio between the AR19G-166-RA and SD5AH4G-1D-1 was 10:0 (namely, the case where the amount of SD5AH4G-1D-1 was 0%).

Figure 6:
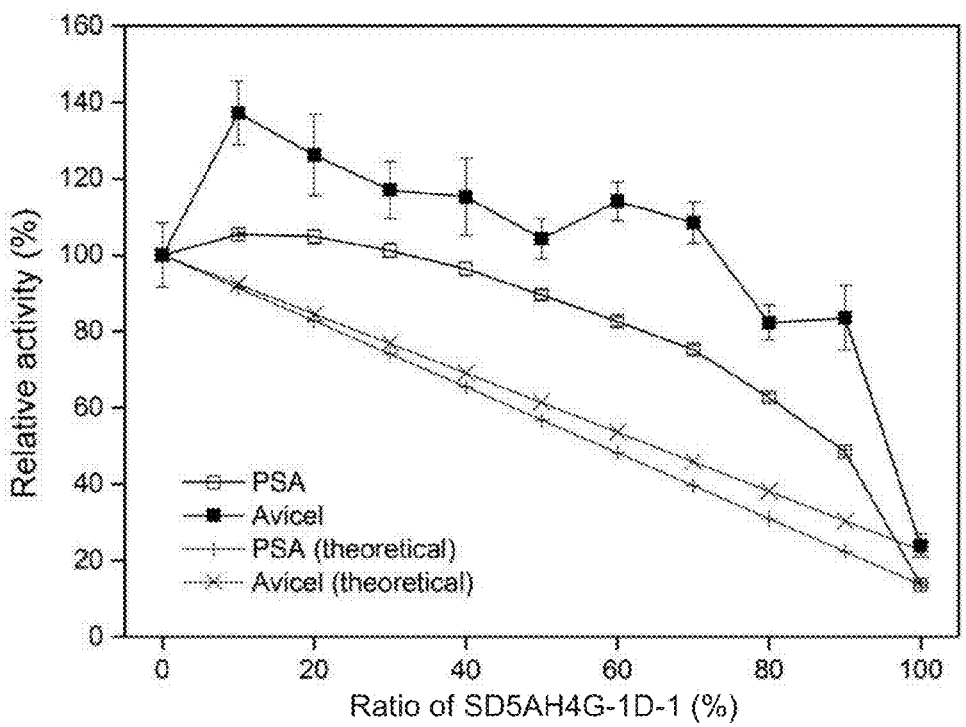
FIG. 6 is a diagram showing the results of measuring the PSA hydrolysis activity and the Avicel hydrolysis activity (pH 5.5, 80° C.) of various enzyme compositions obtained by mixing, in various proportions, the SD5AH4G-1D-1 protein obtained by expressing the SD5AH4G-1D-1 gene in *E. coli* and a GH6 cellobiohydrolase AR19G-166-RA obtained by expression in *E. coli* in Example 1.

The results are shown in FIG. 6. In FIG. 6, the horizontal axis represents the proportion (amount (%)) of SD5AH4G-1D-1 relative to the total amount of enzyme. In the figure, the theoretical values expected for the combination of AR19G-166-RA and SD5AH4G-1D-1 assuming no synergistic effect are shown as dotted lines. The PSA hydrolysis activity and the Avicel hydrolysis activity exceeded the corresponding theoretical value at all of the mixing ratios, confirming a synergistic effect between AR19G-166-RA and SD5AH4G-1D-1. In particular, in the case of the Avicel hydrolysis activity, hydrolysis activity that was superior to that obtained when AR19G-166-RA was used alone was confirmed for those cases where the proportion of SD5AH4G-1D-1 was within a range from 10% to 70%, and the maximum value, observed when the mixing ratio between AR19G-166-RA and SD5AH4G-1D-1 was 9:1, represented an increase in activity of about 40%.

<12> Thermal Stability Measurement of Cellobiohydrolase by Differential Scanning Fluorimetry Differential scanning fluorimetry (DSF) is one of the methods of measuring the thermal denaturation of proteins using a fluorescent dye and a real-time PCR machine, and can be applied to all manner of proteins. The fluorescent dyes used in DSF such as SYPRO Orange emit fluorescence under nonpolar conditions when bound to a hydrophobic region, while the emission is suppressed under the polar conditions produced upon dissolution in water. Usually, the protein structure unfolds at the thermal denaturation temperature, and the internal hydrophobic regions of the protein are exposed at the protein surface. When SYPRO Orange binds to such an exposed hydrophobic region, excitation light having a wavelength of 470 to 480 nm causes emission of a strong fluorescence having a peak near a wavelength of 595 nm. By increasing the temperature of the protein solution at regular intervals in a stepwise manner and measuring the fluorescence intensity, the thermal denaturation temperature (=change point of the fluorescence intensity) can be calculated.

Measurements were performed using a purified enzyme solution prepared by dissolving the purified enzyme SD5AH4G-1D-1 obtained in section <7> above in water at a concentration of 1 mg/mL.

Specifically, 2 μL of 100-fold diluted SYPRO Orange (manufactured by Life Technologies Inc.), 1 μL of the purified enzyme solution with a concentration of 1 mg/mL, 5 μL of a 200 mM acetate buffer (pH 5.5), and 12 μL of either purified water or a solution prepared by mixing purified water and a 10 mM $CaCl_2$ solution in a ratio of 2:1 were added to each well of a 96-well PCR plate (Multiplate 96 Well PCR Plate MLL-9651, manufactured by Bio-Rad Laboratories, Inc.) so that the volume in each well was 20 μL. The PCR plate was sealed with Optical Flat 8-Cap Strips (manufactured by Bio-Rad Laboratories, Inc.), the temperature of each well was increased in steps of 0.2° C. from 30° C. up to 100° C. using a real-time PCR machine (CFX96 Touch Real-Time PCR System, manufactured by Bio-Rad Laboratories, Inc.), and following a pause of 10 seconds after each target temperature was achieved, the fluorescence intensity of each well was measured simultaneously. The SYPRO Orange was excited by a light emitting diode (LED) having a wavelength range of 450 to 490 nm, the emitted light from the SYPRO Orange was passed through a band pass filter having a range of 560 to 580 nm, a CCD camera was used to measure the fluorescence intensity, and the change in fluorescence intensity was plotted as a function of temperature. The thermal denaturation temperature (melting temperature: Tm) was defined as the value at the local minimum of the first derivative of the fluorescence intensity curve plotted as a function of temperature (namely, "−d (Fluorescence)/dT" shown along the Y axis in FIG. 7(B)). Data analysis was conducted using the analysis software CFX Manager (manufactured by Bio-Rad Laboratories, Inc.) supplied with the real-time PCR machine. Each measurement was performed for three independent experiments, and a mean value and a standard error were determined.

Figure 7:
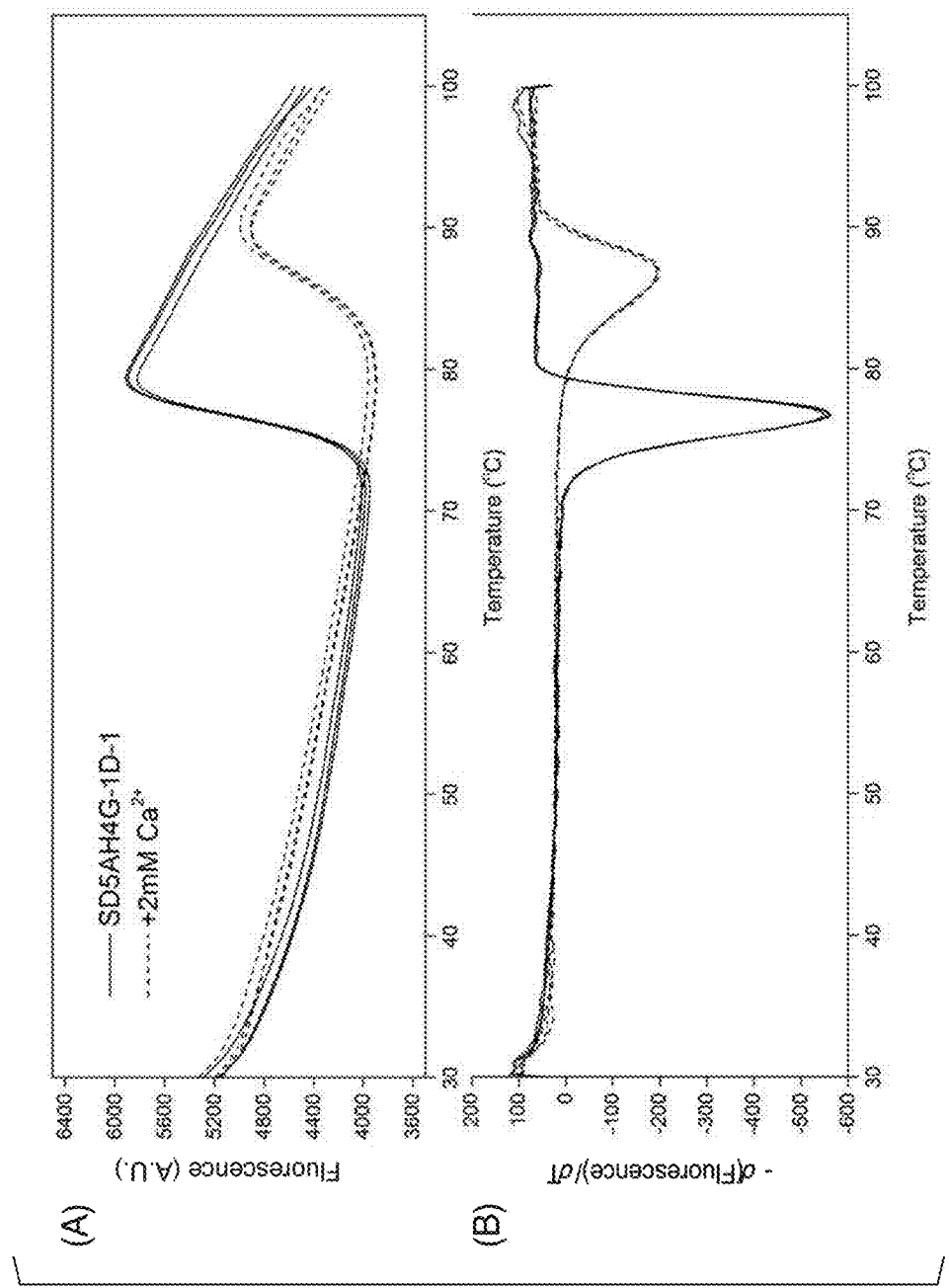
FIG. 7(A) is a diagram showing actual measurement data for the change in the fluorescence intensity of SYPRO Orange that is generated in association with the thermal denaturation exhibited by the SD5AH4G-1D-1 protein obtained by expressing the SD5AH4G-1D-1 gene in *E. coli* in Example 1.
FIG. 7(B) is a diagram showing the first derivative "−d(Fluorescence)/dT" of the fluorescence intensity change curve of FIG. 7(A).

FIG. 7(A) shows the actual measurement data for the change in the fluorescence intensity of SYPRO Orange measured by the DSF method and caused in association with the thermal denaturation exhibited by the SD5AH4G-1D-1 enzyme protein. FIG. 7(B) shows the first derivative "−d (Fluorescence)/dT" of the fluorescence intensity change curve of FIG. 7(A).

The first derivative of the fluorescence intensity of SD5AH4G-1D-1 had a local minimum near 77° C., indicating that thermal denaturation occurs at that temperature. Further, under the conditions including added $CaCl_2$, the local minimum occurred near 87° C. The average values for the thermal denaturation temperature Tm were 76.8±0° C. (no $CaCl_2$ addition) and 87.0±0.1° C. ($CaCl_2$ addition), which were shown that the thermal denaturation temperature was elevated 10.2° C. by calcium ion.

SEQUENCE LISTING

```
<160> NUMBER OF SEQ ID NOS: 10

<210> SEQ ID NO 1
<211> LENGTH: 1146
<212> TYPE: PRT
<213> ORGANISM: Unknown
<220> FEATURE:
<223> OTHER INFORMATION: Amino acid sequence encoded by the open reading
      frame SD5AH4G-1

<400> SEQUENCE: 1

Met Glu Ser Leu Ala Trp Thr Leu Leu Trp Lys Lys Ala Arg Ile Ile
1               5                   10                  15

Phe Leu Ala Phe Ala Leu Val Val Ser Ala Phe Ala Gly Phe Ala Val
                20                  25                  30

Ser Pro His Ser Glu Thr Ala Tyr Ala Gln Thr Asp Pro Gln Val Phe
            35                  40                  45

Lys Asp Arg Phe Leu Gln Leu Tyr Asn Gln Ile Lys Asn Pro Ala Asn
        50                  55                  60

Gly Tyr Phe Ser Pro Glu Gly Ile Pro Tyr His Ser Ile Glu Thr Leu
65                  70                  75                  80

Ile Ser Glu Ala Pro Asp Tyr Gly His Met Thr Thr Ser Glu Ala Phe
                85                  90                  95

Ser Tyr Trp Leu Trp Leu Glu Thr Leu Tyr Gly Tyr Phe Thr Gly Asp
            100                 105                 110

Trp Ser Lys Leu Glu Gln Ala Trp Thr Lys Met Glu Gln Phe Ile Ile
        115                 120                 125

Pro Ser Ser Thr Glu Gln Pro Thr Met Gly Ala Tyr Asn Pro Ser Ser
130                 135                 140

Pro Ala Thr Tyr Ala Pro Glu His Pro Tyr Pro Asp Arg Tyr Pro Thr
145                 150                 155                 160

Leu Leu Asn Asn Ser Val Pro Ala Gly Gln Asp Pro Leu Asp Ala Glu
                165                 170                 175

Leu Lys Ala Thr Tyr Gly Asn Asn Val Thr Tyr Leu Met His Trp Leu
            180                 185                 190

Leu Asp Val Asp Asn Trp Tyr Gly Phe Gly Asn Leu Leu Asn Pro Ser
        195                 200                 205

His Thr Ala Thr Tyr Val Asn Thr Phe Gln Arg Gly Glu Gln Glu Ser
    210                 215                 220

Val Trp Glu Ala Ile Thr His Pro Ser Gln Asp Asn Phe Arg Phe Gly
225                 230                 235                 240

Lys Pro Asn Glu Gly Phe Val Thr Leu Phe Val Lys Asp Asn Gly Thr
                245                 250                 255

Pro Ala Gln Gln Trp Arg Tyr Thr Ala Ala Ser Asp Ala Asp Ala Arg
            260                 265                 270
```

```
Ala Ile Gln Val Met Tyr Trp Ala Lys Gln Leu Gly Tyr Asn Asn Gln
        275                 280                 285

Thr Tyr Leu Asp Lys Ala Arg Lys Met Gly Asp Tyr Leu Arg Tyr Thr
    290                 295                 300

Leu Phe Asp Lys Tyr Phe Gln Gln Ile Gly Ser Ala Asn Asp Gly Ser
305                 310                 315                 320

Pro Ser Pro Gly Ser Gly Lys Asn Ser Ala His Tyr Leu Leu Ser Trp
                325                 330                 335

Tyr Thr Ala Trp Gly Gly Leu Gly Ser Gly Gly Asn Trp Ala Trp
                340                 345                 350

Arg Ile Gly Ser Ser His Ala His Gln Gly Tyr Gln Asn Pro Val Ala
                355                 360                 365

Ala Tyr Ala Leu Ser Ala Gly Gly Leu Ala Pro Arg Ser Ala Thr Ala
        370                 375                 380

Gln Thr Asp Trp Ala Thr Ser Leu Gln Arg Gln Leu Glu Phe Tyr Thr
385                 390                 395                 400

Trp Leu Gln Ser Ser Glu Gly Ala Ile Gly Gly Ala Thr Asn Ser
                405                 410                 415

Val Gly Gly Ser Tyr Gln Pro Tyr Pro Ser Gly Arg Ser Thr Phe Tyr
                420                 425                 430

Gly Met Val Tyr Asp Glu Ala Pro Val Tyr Arg Asp Pro Pro Ser Asn
            435                 440                 445

Ser Trp Phe Gly Phe Gln Ala Trp Ser Val Glu Arg Val Ala Glu Leu
    450                 455                 460

Tyr Tyr Ile Leu Ala Ser Ser Gly Asn Thr Asn Thr Gln Gln Phe Gln
465                 470                 475                 480

Met Val Lys Asn Ile Val Thr Lys Trp Val Asp Trp Ala Leu Asp Tyr
                485                 490                 495

Thr Phe Val Asn Gln Arg Pro Val Thr Asp Ala Gln Gly Tyr Phe Leu
            500                 505                 510

Thr Ser Ser Gly Ser Arg Val Leu Gly Gly Asn Asn Pro Gln Ile Ala
        515                 520                 525

Thr Val Ser Asp Pro Gly Gln Phe Tyr Ile Pro Ser Thr Leu Glu Trp
    530                 535                 540

Gln Gly Gln Pro Asp Thr Trp Asn Gly Tyr Ala Asn Tyr Thr Gly Asn
545                 550                 555                 560

Pro Asn Phe His Ala Ile Ala Lys Asp Pro Gly Gln Asp Val Gly Val
                565                 570                 575

Thr Gly Asn Tyr Ile Lys Leu Leu Thr Phe Phe Ala Ala Ala Thr Lys
            580                 585                 590

Ala Glu Thr Gly Asn Tyr Thr Ala Leu Gly Ser Gln Ala Leu Asn Val
        595                 600                 605

Ala Glu Gln Leu Leu Asn Val Leu Trp Asn Phe Asn Asp Gly Val Gly
    610                 615                 620

Ile Val Arg Pro Glu Gln Arg Pro Asp Tyr Phe Arg Tyr Phe Thr Lys
625                 630                 635                 640

Glu Ile Tyr Phe Pro Asn Gly Trp Ser Gly Thr Tyr Gly Gln Gly Asn
                645                 650                 655

Thr Ile Pro Gly Pro Gly Ala Val Pro Ser Asp Pro Ser Lys Gly Gly
            660                 665                 670

Asn Gly Val Tyr Ile Ser Tyr Ala Glu Leu Arg Pro Lys Ile Lys Gln
        675                 680                 685
```

```
Asp Pro Lys Trp Ser Tyr Leu Glu Asn Leu Tyr Asn Thr Ser Tyr Asn
    690             695                 700
Pro Ser Thr Gly Arg Trp Glu Asn Gly Val Pro Thr Phe Thr Tyr His
705             710                 715                 720
Arg Phe Trp Ala Gln Val Asp Val Ala Thr Ala Tyr Ala Glu Phe Ala
            725                 730                 735
Arg Leu Ile Gly Gly Leu Gly Ala Ser Pro Thr Pro Thr Pro Ser Ala
                740                 745                 750
Thr Pro Thr Pro Thr Pro Thr Pro Thr Pro Ser Ala Thr Pro Thr Pro
            755                 760                 765
Thr Pro Thr Pro Thr Pro Thr Pro Thr Pro Thr Pro Thr Pro Thr Pro
770             775                 780
Thr Pro Thr Ala Thr Pro Thr Pro Thr Pro Ile Pro Thr Pro Thr Val
785             790                 795                 800
Thr Pro Thr Pro Thr Pro Met Pro Ser Ala Ser Gly Thr Leu Arg Val
                805                 810                 815
Glu Tyr Arg Val Gly Asp Ser Ser Ala Thr Asp Asn Gln Met Lys Pro
            820                 825                 830
Gln Leu Arg Ile Val Asn Thr Gly Ser Gln Ala Val Pro Leu Thr Glu
            835                 840                 845
Leu Lys Val Arg Tyr Trp Tyr Thr Lys Asn Ser Thr Gln Ala Glu Gln
850                 855                 860
Tyr Phe Cys Asp Trp Ala Gln Ile Gly Cys Ser Asn Ile Arg Ala Gln
865                 870                 875                 880
Phe Val Ser Leu Ser Gln Pro Val Ser Gly Ala Asp Ser Tyr Ile Glu
                885                 890                 895
Leu Ser Phe Thr Gly Gly Ser Ile Pro Ala Gly Gly Asn Thr Gly Glu
                900                 905                 910
Ile Gln Asn Arg Ile His Phe Thr Asn Trp Met Asn Tyr Asn Glu Ala
                915                 920                 925
Asp Asp Trp Ser Tyr Asn Gly Ala Gln Thr Thr Trp Gly Pro Ser Thr
            930                 935                 940
Arg Ile Thr Leu Tyr Arg Asn Gly Val Leu Val Trp Gly Thr Glu Pro
945                 950                 955                 960
Gly Gly Ser Ser Thr Pro Thr Pro Thr Pro Ser Ala Thr Pro Thr Pro
                965                 970                 975
Thr Pro Thr Pro Thr Pro Ser Ala Ala Pro Thr Pro Thr Pro Thr Pro
            980                 985                 990
Ser Ala Gly Gly Ser Leu Val Val Gln Tyr Arg Ala Ala Asp Thr Asn
            995                 1000                1005
Ala Gly Asp Asn Gln Leu Lys Pro His Phe Arg Ile Val Asn Arg
        1010                1015                1020
Gly Thr Thr Ser Val Pro Leu Ser Glu Leu Ser Ile Arg Tyr Trp
        1025                1030                1035
Tyr Thr Val Asp Gly Asp Lys Pro Gln Val Phe Asn Cys Asp Trp
        1040                1045                1050
Ala Gln Val Gly Cys Ser Asn Val Arg Gly Ser Phe Val Lys Leu
        1055                1060                1065
Ser Thr Gly Arg Thr Gly Ala Asp Tyr Tyr Val Glu Ile Thr Phe
        1070                1075                1080
Thr Ser Gly Ala Gly Ser Leu Ala Pro Gly Ala Ser Ser Gly Asp
        1085                1090                1095
```

```
Ile Gln Ala Arg Ile Asn Lys Asn Asp Trp Thr Asn Tyr Asn Glu
1100                1105                1110

Ala Asn Asp Tyr Ser Tyr Asp Pro Thr Lys Thr Ser Phe Ala Asp
1115                1120                1125

Trp Asn Arg Val Thr Leu Tyr Arg Asn Gly Gln Leu Val Trp Gly
1130                1135                1140

Val Glu Pro
1145

<210> SEQ ID NO 2
<211> LENGTH: 703
<212> TYPE: PRT
<213> ORGANISM: Unknown
<220> FEATURE:
<223> OTHER INFORMATION: Amino acid sequence of SD5AH4G-1D-1

<400> SEQUENCE: 2

Asp Pro Gln Val Phe Lys Asp Arg Phe Leu Gln Leu Tyr Asn Gln Ile
1               5                   10                  15

Lys Asn Pro Ala Asn Gly Tyr Phe Ser Pro Glu Gly Ile Pro Tyr His
            20                  25                  30

Ser Ile Glu Thr Leu Ile Ser Glu Ala Pro Asp Tyr Gly His Met Thr
        35                  40                  45

Thr Ser Glu Ala Phe Ser Tyr Trp Leu Trp Leu Glu Thr Leu Tyr Gly
50                  55                  60

Tyr Phe Thr Gly Asp Trp Ser Lys Leu Glu Gln Ala Trp Thr Lys Met
65                  70                  75                  80

Glu Gln Phe Ile Ile Pro Ser Ser Thr Glu Gln Pro Thr Met Gly Ala
                85                  90                  95

Tyr Asn Pro Ser Ser Pro Ala Thr Tyr Ala Pro Glu His Pro Tyr Pro
            100                 105                 110

Asp Arg Tyr Pro Thr Leu Leu Asn Asn Ser Val Pro Ala Gly Gln Asp
        115                 120                 125

Pro Leu Asp Ala Glu Leu Lys Ala Thr Tyr Gly Asn Asn Val Thr Tyr
130                 135                 140

Leu Met His Trp Leu Leu Asp Val Asp Asn Trp Tyr Gly Phe Gly Asn
145                 150                 155                 160

Leu Leu Asn Pro Ser His Thr Ala Thr Tyr Val Asn Thr Phe Gln Arg
                165                 170                 175

Gly Glu Gln Glu Ser Val Trp Glu Ala Ile Thr His Pro Ser Gln Asp
            180                 185                 190

Asn Phe Arg Phe Gly Lys Pro Asn Glu Gly Phe Val Thr Leu Phe Val
        195                 200                 205

Lys Asp Asn Gly Thr Pro Ala Gln Gln Trp Arg Tyr Thr Ala Ala Ser
210                 215                 220

Asp Ala Asp Ala Arg Ala Ile Gln Val Met Tyr Trp Ala Lys Gln Leu
225                 230                 235                 240

Gly Tyr Asn Asn Gln Thr Tyr Leu Asp Lys Ala Arg Lys Met Gly Asp
                245                 250                 255

Tyr Leu Arg Tyr Thr Leu Phe Asp Lys Tyr Phe Gln Gln Ile Gly Ser
            260                 265                 270

Ala Asn Asp Gly Ser Pro Ser Pro Gly Ser Gly Lys Asn Ser Ala His
        275                 280                 285

Tyr Leu Leu Ser Trp Tyr Thr Ala Trp Gly Gly Gly Leu Gly Ser Gly
290                 295                 300
```

-continued

```
Gly Asn Trp Ala Trp Arg Ile Gly Ser Ser His Ala His Gln Gly Tyr
305                 310                 315                 320

Gln Asn Pro Val Ala Ala Tyr Ala Leu Ser Ala Gly Gly Leu Ala Pro
            325                 330                 335

Arg Ser Ala Thr Ala Gln Thr Asp Trp Ala Thr Ser Leu Gln Arg Gln
        340                 345                 350

Leu Glu Phe Tyr Thr Trp Leu Gln Ser Ser Glu Gly Ala Ile Gly Gly
    355                 360                 365

Gly Ala Thr Asn Ser Val Gly Gly Ser Tyr Gln Pro Tyr Pro Ser Gly
370                 375                 380

Arg Ser Thr Phe Tyr Gly Met Val Tyr Asp Glu Ala Pro Val Tyr Arg
385                 390                 395                 400

Asp Pro Pro Ser Asn Ser Trp Phe Gly Phe Gln Ala Trp Ser Val Glu
            405                 410                 415

Arg Val Ala Glu Leu Tyr Tyr Ile Leu Ala Ser Ser Gly Asn Thr Asn
        420                 425                 430

Thr Gln Gln Phe Gln Met Val Lys Asn Ile Val Thr Lys Trp Val Asp
    435                 440                 445

Trp Ala Leu Asp Tyr Thr Phe Val Asn Gln Arg Pro Val Thr Asp Ala
450                 455                 460

Gln Gly Tyr Phe Leu Thr Ser Ser Gly Ser Arg Val Leu Gly Gly Asn
465                 470                 475                 480

Asn Pro Gln Ile Ala Thr Val Ser Asp Pro Gly Gln Phe Tyr Ile Pro
            485                 490                 495

Ser Thr Leu Glu Trp Gln Gly Gln Pro Asp Thr Trp Asn Gly Tyr Ala
        500                 505                 510

Asn Tyr Thr Gly Asn Pro Asn Phe His Ala Ile Ala Lys Asp Pro Gly
    515                 520                 525

Gln Asp Val Gly Val Thr Gly Asn Tyr Ile Lys Leu Leu Thr Phe Phe
530                 535                 540

Ala Ala Ala Thr Lys Ala Glu Thr Gly Asn Tyr Thr Ala Leu Gly Ser
545                 550                 555                 560

Gln Ala Leu Asn Val Ala Glu Gln Leu Leu Asn Val Leu Trp Asn Phe
            565                 570                 575

Asn Asp Gly Val Gly Ile Val Arg Pro Glu Gln Arg Pro Asp Tyr Phe
        580                 585                 590

Arg Tyr Phe Thr Lys Glu Ile Tyr Phe Pro Asn Gly Trp Ser Gly Thr
    595                 600                 605

Tyr Gly Gln Gly Asn Thr Ile Pro Gly Pro Gly Ala Val Pro Ser Asp
610                 615                 620

Pro Ser Lys Gly Gly Asn Gly Val Tyr Ile Ser Tyr Ala Glu Leu Arg
625                 630                 635                 640

Pro Lys Ile Lys Gln Asp Pro Lys Trp Ser Tyr Leu Glu Asn Leu Tyr
            645                 650                 655

Asn Thr Ser Tyr Asn Pro Ser Thr Gly Arg Trp Glu Asn Gly Val Pro
        660                 665                 670

Thr Phe Thr Tyr His Arg Phe Trp Ala Gln Val Asp Val Ala Thr Ala
    675                 680                 685

Tyr Ala Glu Phe Ala Arg Leu Ile Gly Gly Leu Gly Ala Ser Pro
690                 695                 700
```

<210> SEQ ID NO 3
<211> LENGTH: 3441
<212> TYPE: DNA
<213> ORGANISM: Unknown
<220> FEATURE:
<223> OTHER INFORMATION: Amino acid sequence encoded by the open reading
      frame SD5AH4G-1

<400> SEQUENCE: 3

| | | | | | |
|---|---|---|---|---|---|
| atggaatcgc | ttgcatggac | gctattatgg | aagaaagcaa | gaattatctt | tcttgctttc | 60 |
| gcgcttgtcg | tctccgcctt | cgcgggcttc | gcagtgtctc | ctcatagcga | aaccgcttac | 120 |
| gcccagacgg | acccgcaggt | tttcaaggac | aggtttttgc | agctgtacaa | ccaaatcaaa | 180 |
| aatccggcga | acggttactt | ttcgccggaa | ggcattcctt | atcactccat | cgaaacgttg | 240 |
| atttcggaag | ctccccgacta | tgggcatatg | acgacatcgg | aagcgttcag | ttattggctc | 300 |
| tggctggaaa | cgctatatgg | ttacttcacc | ggtgactggt | cgaaactgga | acaggcctgg | 360 |
| acgaaaatgg | aacaattcat | tattccgagc | tcgaccgaac | agccgacgat | gggggcttac | 420 |
| aacccgtcaa | gtccagctac | ttacgcgccg | aacatccgt | atccggaccg | gtatccaact | 480 |
| ttgctgaaca | attccgtgcc | agcaggacag | gacccactgg | atgcggaact | caaagcgacg | 540 |
| tacggtaata | acgtgacgta | tttgatgcac | tggctgctcg | acgtggacaa | ctggtacggc | 600 |
| tcggcaacc | tgttgaaccc | gtcgcatacg | gcgacctacg | tcaacacgtt | ccagcgcggc | 660 |
| gaacaggaat | cggtctggga | ggcgatcaca | catccgtcgc | aggacaattt | ccggttcgga | 720 |
| aaaccgaatg | aaggttttgt | gacgctgttc | gtaaaagata | acggaacgcc | tgcccagcaa | 780 |
| tggcgttata | cggcagcctc | tgacgccgac | gcacgcgcca | ttcaggtgat | gtattgggcg | 840 |
| aagcagctgg | gatacaacaa | ccagacctat | ctggataagg | cgcgcaagat | gggcgactat | 900 |
| ctgcgctata | cactgttcga | caagtatttc | caacaaatcg | gcagcgcaaa | cgacggttct | 960 |
| ccgagcccgg | gcagcggtaa | aaactctgcg | cattacctct | tgtcttggta | cacggcctgg | 1020 |
| ggcgtggtc | tcggctccgg | cggcaattgg | gcttggagaa | tcggatcgag | ccatgctcat | 1080 |
| cagggttatc | aaaatcctgt | cgctgcttat | gcgctttctg | ctggcggact | ggcgccgcgt | 1140 |
| tccgcaacgg | cacagacaga | ctgggcgacg | tcgttgcaac | gtcagcttga | attctatacg | 1200 |
| tggctgcaat | cgagcgaagg | cgccatcggc | ggcgggcga | ccaacagcgt | cggggcagc | 1260 |
| tatcagccgt | atccttccgg | tcgcagcaca | ttctacggca | tggtttacga | tgaagcgccg | 1320 |
| gtttatcgcg | atccgccttc | gaactcgtgg | ttcggcttcc | aagcgtggtc | cgtcgaacgc | 1380 |
| gtcgcggaac | tgtattacat | cttgccagc | agcggaaata | ccaatacgca | gcaattccag | 1440 |
| atggttaaaa | acatcgtcac | caaatggggtt | gactgggcgc | ttgactatac | gttcgtgaac | 1500 |
| caacgcccgg | ttacggatgc | tcaggggtat | ttcctgacga | gcagcggcag | ccgtgtctta | 1560 |
| ggcggcaaca | atccgcagat | cgccacggtt | tccgatcccg | gtcagttcta | tattccgtcg | 1620 |
| acgctggaat | ggcagggtca | accggacaca | tggaacggat | atgccaacta | tcgggcaat | 1680 |
| cccaatttcc | atgcgatagc | aaaagacccc | ggccaagacg | tcggcgtcac | cggcaactat | 1740 |
| atcaagctgc | tgacgttctt | tgccgcagcc | acgaaagcgg | agacggggaa | ctacactgct | 1800 |
| ctcggaagcc | aggccttgaa | tgtcgccgaa | cagttgctga | acgtgctttg | gaattttaac | 1860 |
| gacggtgtgg | ggattgtccg | tcccgaacaa | cgccccgact | acttccgcta | ttttacgaag | 1920 |
| gaaatttact | tcccgaacgg | ctggagcggc | acgtacggac | aggcaatac | cattcctggg | 1980 |
| ccggggcgcg | ttccttccga | tccgtcgaaa | ggcggaaacg | gcgtttatat | cagctacgcc | 2040 |
| gaactgcgtc | cgaagatcaa | gcaagacccg | aaatggtcgt | accttgagaa | tctatacaac | 2100 |

| | |
|---|---:|
| acttcgtata atccgtccac aggtcgctgg gaaaacggtg ttccgacgtt cacgtatcac | 2160 |
| cgtttctggg cgcaggtcga tgtggcgacg gcctatgctg aatttgctcg cttgatcggc | 2220 |
| ggtttgggcg cttcgccgac accgacgccg agcgcgacac cgacgccgac accgacaccg | 2280 |
| acgccgagcg cgacaccgac gccgacaccg agccgacaca caacaccgac gccgacaccg | 2340 |
| acaccaacgc cgacgccgac tgcgacaccg acgccgacgc cgataccgac accgacggtg | 2400 |
| acaccgacac cgacgccgat gcctagcgcg agcggcaccc tgcgcgtcga gtatcgcgtg | 2460 |
| ggcgactcta gcgccaccga caaccagatg aaaccgcagc tgcgcatcgt caacaccggc | 2520 |
| tcgcaagccg tgccgctgac cgagctgaag gtgcgctact ggtacacgaa gaactcgacg | 2580 |
| caggccgaac agtacttctg cgactgggcg cagatcggct gctcgaacat ccgggcgcag | 2640 |
| ttcgtgtcgc tgtcgcagcc ggtcagcggg gcggacagca catcgagct gagcttcacg | 2700 |
| ggcggaagca ttccggcggg aggcaacacg ggcgaaattc agaaccggat tcacttcacg | 2760 |
| aactggatga actacaacga agcggacgac tggtcgtaca acgggcgca gacgacgtgg | 2820 |
| gggccgtcga cgcggattac gctgtatcgc aacggcgtgc tggtatgggg cacggagccg | 2880 |
| ggcggatcgt cgacgccgac accgacaccg agcgcgacac cgacgccgac gccaacgcct | 2940 |
| acgccgagcg cggcgcccac accgacgccg agccgtcgg ccggcggcag cctggtcgtg | 3000 |
| cagtatcgcg cggcagacac gaatgcgggc gacaaccagc tgaagccgca cttcaggatc | 3060 |
| gtgaaccgcg gacgacgag cgtgccgctg tcggagcttt cgattcggta ctggtacacg | 3120 |
| gtggacgggg acaagccgca agtgtttaac tgcgactggg cgcaggtggg ttgctcgaac | 3180 |
| gtgcggggca gcttcgtgaa gctttcgacg ggccggacgg gggcggacta ctacgttgag | 3240 |
| atcacgttca cgtcgggcgc gggcagcctg gcgcctgggg cgagcagcgg agacattcag | 3300 |
| gcgcggatca acaagaacga ctggacgaac tacaatgagg cgaacgacta ctcgtatgat | 3360 |
| ccgacgaaga cgagttttgc ggattggaac cgggtgacgc tgtatcgcaa cggtcagctc | 3420 |
| gtctggggcg tcgaaccgta a | 3441 |

<210> SEQ ID NO 4
<211> LENGTH: 2109
<212> TYPE: DNA
<213> ORGANISM: Unknown
<220> FEATURE:
<223> OTHER INFORMATION: Amino acid sequence of SD5AH4G-1D-1

<400> SEQUENCE: 4

| | |
|---|---:|
| gacccgcagg ttttcaagga caggtttttg cagctgtaca accaaatcaa aaatccggcg | 60 |
| aacggttact tttcgccgga aggcattcct tatcactcca tcgaaacgtt gatttcggaa | 120 |
| gctcccgact atgggcatat gacgacatcg gaagcgttca gttattggct ctggctggaa | 180 |
| acgctatatg gttacttcac cggtgactgg tcgaaactgg aacaggcctg gacgaaaatg | 240 |
| gaacaattca ttattccgag ctcgaccgaa cagccgacga tggggctta caacccgtca | 300 |
| agtccagcta cttacgcgcc ggaacatccg tatccggacc ggtatccaac tttgctgaac | 360 |
| aattccgtgc cagcaggaca ggaccccactg gatgcgaac tcaaagcgac gtacggtaat | 420 |
| aacgtgacgt atttgatgca ctggctgctc gacgtggaca actggtacgg cttcggcaac | 480 |
| ctgttgaacc cgtcgcatac ggcgacctac gtcaacacgt tccagcgcgg cgaacaggaa | 540 |
| tcggtctggg aggcgatcac acatccgtcg caggacaatt tccggttcgg aaaaccgaat | 600 |
| gaaggttttg tgacgctgtt cgtaaaagat aacggaacgc ctgcccagca atggcgttat | 660 |

-continued

```
acggcagcct ctgacgccga cgcacgcgcc attcaggtga tgtattgggc gaagcagctg    720
ggatacaaca accagaccta tctggataag gcgcgcaaga tgggcgacta tctgcgctat    780
acactgttcg acaagtattt ccaacaaatc ggcagcgcaa acgacggttc tccgagcccg    840
ggcagcggta aaaactctgc gcattacctc ttgtcttggt acacggcctg gggcggtggt    900
ctcggctccg gcggcaattg ggcttggaga atcggatcga gccatgctca tcagggttat    960
caaaatcctg tcgctgctta tgcgctttct gctggcggac tggcgccgcg ttccgcaacg   1020
gcacagacag actgggcgac gtcgttgcaa cgtcagcttg aattctatac gtggctgcaa   1080
tcgagcgaag gcgccatcgg cggcggggcg accaacagcg tcggggggcag ctatcagccg   1140 tatccttccg gtcgcagcac attctacggc atggtttacg atgaagcgcc ggtttatcgc   1200
gatccgcctt cgaactcgtg gttcggcttc aagcgtggt ccgtcgaacg cgtcgcggaa    1260
ctgtattaca tcttggccag cagcggaaat accaatacgc agcaattcca gatggttaaa   1320
aacatcgtca ccaaatgggt tgactgggcg cttgactata cgttcgtgaa ccaacgcccg   1380
gttacggatg ctcaggggta tttcctgacg agcagcggca gccgtgtctt aggcggcaac   1440
aatccgcaga tcgccacggt ttccgatccc ggtcagttct atattccgtc gacgctggaa   1500
tggcagggtc aaccggacac atggaacgga tatgccaact atacgggcaa tcccaatttc   1560
catgcgatag caaaagaccc cggccaagac gtcggcgtca ccggcaacta tcaagctg    1620 ctgacgttct tgccgcagc cacgaaagcg gagacgggga actacactgc tctcggaagc   1680
caggccttga atgtcgccga acagttgctg aacgtgcttt ggaatttaa cgacggtgtg   1740 gggattgtcc gtcccgaaca acgccccgac tacttccgct attttacgaa ggaaatttac   1800
ttcccgaacg gctggagcgg cacgtacgga cagggcaata ccattcctgg gccgggcgcg   1860
gttccttccg atccgtcgaa aggcggaaac ggcgtttata tcagctacgc cgaactgcgt   1920
ccgaagatca agcaagaccc gaaatggtcg taccttgaga atctatacaa cacttcgtat   1980
aatccgtcca caggtcgctg ggaaaacggt gttccgacgt tcacgtatca ccgtttctgg   2040
gcgcaggtcg atgtggcgac ggcctatgct gaatttgctc gcttgatcgg cggtttgggc   2100
gcttcgccg                                                          2109
```

<210> SEQ ID NO 5
<211> LENGTH: 18
<212> TYPE: DNA
<213> ORGANISM: Artificial Sequence
<220> FEATURE:
<223> OTHER INFORMATION: Primer; homologous (identical) with the partial
      sequence composed of the nucleotides from positions 130 to 147 of
      the nucleotide sequence represented by SEQ ID NO: 3

<400> SEQUENCE: 5
gacccgcagg ttttcaag                                                   18

<210> SEQ ID NO 6
<211> LENGTH: 17
<212> TYPE: DNA
<213> ORGANISM: Artificial Sequence
<220> FEATURE:
<223> OTHER INFORMATION: Primer; complementary with the partial sequence
      composed of the nucleotides from positions 2,222 to 2,238 of the
      nucleotide sequence represented by SEQ ID NO: 3

<400> SEQUENCE: 6
cggcgaagcg cccaaac                                                    17

-continued

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gtgatggacc cgcaggtttt caag                                              24

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
gtaagcttac ggcgaagcgc ccaaac                                            26

<210> SEQ ID NO 9
<211> LENGTH: 1158
<212> TYPE: PRT
<213> ORGANISM: Unknown
<220> FEATURE:
<223> OTHER INFORMATION: Cellulose 1,4-beta-cellobiosidase of
      paenibacillus mucilaginosus

<400> SEQUENCE: 9

Met His Asp Met Thr Lys Lys Asn Thr Gly Leu Tyr Gln Arg Leu Gly
1               5                   10                  15

Lys Leu Leu Leu Ala Ser Ser Leu Ser Leu Pro Leu Phe Ser Val Leu
            20                  25                  30

Ala Val Thr Ser Pro Ala Asn Leu Ala Tyr Ala Ala Glu Asp Thr Thr
        35                  40                  45

Asn Lys Thr Arg Phe Leu Thr Leu Tyr Asn Gln Ile Lys Asp Pro Ala
50                  55                  60

Asn Gly Tyr Phe Ser Pro Glu Gly Ile Pro Tyr His Ala Val Glu Thr
65                  70                  75                  80

Leu Leu Ser Glu Ala Pro Asp His Gly His Met Thr Thr Ser Glu Ala
                85                  90                  95

Tyr Ser Tyr Trp Leu Trp Leu Glu Ala Leu Tyr Gly His His Thr Gly
            100                 105                 110

Asn Trp Thr Arg Leu Glu Gln Ala Trp Asp Asn Met Glu Gln Tyr Ile
        115                 120                 125

Ile Pro Asn Ala Ser Glu Gln Pro Thr Met Ser Gly Tyr Asn Pro Ala
    130                 135                 140

Ser Pro Ala Thr Tyr Ala Pro Glu His Arg Gln Pro Asp Gln Tyr Pro
145                 150                 155                 160

Ser Gln Leu Gly Ser Ser Val Thr Ala Gly Lys Asp Pro Leu Asp Ala
                165                 170                 175

Glu Leu Lys Ala Thr Tyr Gly Ser Asn Gln Thr Tyr Leu Met His Trp
            180                 185                 190

Leu Val Asp Val Asp Asn Trp Tyr Gly Phe Gly Asn Ser Leu Asn Pro
        195                 200                 205

Ser His Thr Ala Thr Tyr Ile Asn Thr Phe Gln Arg Gly Glu Gln Glu
    210                 215                 220

Ser Val Trp Glu Ala Ile Pro His Pro Ser Gln Glu Thr Phe Gln Phe
225                 230                 235                 240

-continued

Gly Lys Pro Gly Glu Gly Phe Ala Thr Leu Phe Val Lys Asp Ser Gly
                245                 250                 255

Ala Pro Ala Lys Gln Trp Arg Tyr Thr Asp Ala Thr Asp Ala Asp Ala
            260                 265                 270

Arg Val Val Gln Val Met Tyr Trp Ala Lys Ser Leu Gly Tyr Ser Asn
        275                 280                 285

Pro Val Tyr Ile Glu Lys Ala Lys Lys Met Gly Asp Tyr Leu Arg Tyr
    290                 295                 300

Gly Met Tyr Asp Lys Tyr Phe Gln Gln Ile Gly Ser Ala Ala Asp Gly
305                 310                 315                 320

Thr Pro Ser Pro Gly Thr Gly Lys Asp Ser Ser His Tyr Leu Met Ala
                325                 330                 335

Trp Tyr Thr Ala Trp Gly Gly Ile Gly Ser Asn Trp Ala Trp Arg
            340                 345                 350

Ile Gly Ala Ser His Asn His Gln Ala Tyr Gln Asn Pro Met Ala Ala
        355                 360                 365

Tyr Ala Leu Ser Glu Gly Gly Leu Ala Pro Lys Ser Pro Thr Ala Lys
    370                 375                 380

Gln Asp Trp Glu Thr Ser Leu Lys Arg Gln Leu Glu Phe Tyr Thr Trp
385                 390                 395                 400

Leu Gln Ser Ser Glu Gly Gly Ile Gly Gly Ala Thr Asn Ser Lys
                405                 410                 415

Gly Gly Thr Tyr Ala Pro Tyr Pro Ala Gly Val Ser Thr Phe Tyr Gly
            420                 425                 430

Met Ala Tyr Glu Asp Ala Pro Val Tyr His Asp Pro Ser Asn Thr
        435                 440                 445

Trp Phe Gly Phe Gln Ala Trp Pro Val Glu Arg Ile Ala Glu Tyr Tyr
    450                 455                 460

Tyr Ala Met Ala Ala Lys Gly Asp Thr Ala Ser Glu Asn Phe Lys Met
465                 470                 475                 480

Ala Lys Arg Val Met Asp Gln Trp Val Lys Trp Ala Leu Ala Tyr Thr
                485                 490                 495

Phe Val Asp Lys Lys Pro Val Thr Asp Ala Asp Gly Tyr Phe Leu Asn
            500                 505                 510

Ser Ser Gly Gln Lys Ile Leu Gly Gly Ala Asn Pro Gln Val Ala Thr
        515                 520                 525

Thr Pro Ala Pro Gly Gln Phe Tyr Ile Leu Gly Gly Gln Glu Trp Thr
    530                 535                 540

Gly Gln Pro Asp Ser Trp Lys Gly Phe Ser Ser Phe Thr Gly Asn Pro
545                 550                 555                 560

Asn Tyr His Val Ile Ala Lys Gly Thr Ser Gln Asp Thr Gly Val Leu
                565                 570                 575

Gly Ser Tyr Ile Lys Leu Leu Thr Phe Tyr Ala Ala Gly Thr Gln Ala
            580                 585                 590

Glu Asn Asn Gly Thr Leu Ser Ala Ala Gly Ala Gln Ala Lys Thr Thr
        595                 600                 605

Ala Glu Gln Leu Leu Asn Val Ala Trp Asn His Asn Asp Gly Ile Gly
    610                 615                 620

Ile Ala Val Pro Glu Lys Arg Gly Asp Tyr Ser Arg Tyr Phe Thr Lys
625                 630                 635                 640

Glu Ile Tyr Phe Pro Ser Gly Trp Ser Gly Thr Tyr Gly Gln Gly Asn
                645                 650                 655

```
Ala Leu Pro Gly Thr Gly Ala Val Pro Ser Asp Pro Ala Lys Gly Gly
            660                 665                 670

Asn Gly Val Tyr Leu Ser Tyr Ser Glu Leu Arg Pro Lys Ile Lys Gln
            675                 680                 685

Asp Pro Lys Trp Pro Tyr Leu Glu Asn Leu Tyr Lys Ser Ser Tyr Asp
            690                 695                 700

Pro Val Thr Lys Lys Trp Thr Asn Gly Glu Pro Thr Phe Thr Tyr His
705                 710                 715                 720

Arg Phe Trp Ala Gln Val Asp Met Ala Thr Ala Tyr Ala Glu Tyr Ser
            725                 730                 735

Arg Leu Phe Gly Ser Gly Ser Thr Thr Pro Ser Val Pro Gly Ala Pro
            740                 745                 750

Ala Gly Leu Thr Ala Ala Ala Gly Asp Ala Lys Ala Thr Leu Thr Trp
            755                 760                 765

Ser Ala Ser Ala Gly Ala Ala Ser Tyr Asn Val Lys Arg Ala Thr Thr
            770                 775                 780

Ala Gly Gly Pro Tyr Thr Thr Val Ser Thr Gly Val Thr Ala Thr Gly
785                 790                 795                 800

Phe Thr Asp Thr Ala Val Thr Asn Gly Thr Thr Tyr Tyr Val Val
            805                 810                 815

Ser Ala Val Asn Ser Val Gly Glu Ser Pro Asn Ser Ala Gln Val Ser
            820                 825                 830

Val Lys Lys Pro Gln Ala Gly Thr Ala Ala Val Pro Ala Ala Pro Ala
            835                 840                 845

Gly Leu Ser Ala Ala Ser Gly Asp Ala Lys Val Thr Leu Gly Trp Asn
850                 855                 860

Ala Pro Ala Gly Ala Ala Ser Tyr Asn Val Lys Arg Ala Thr Thr Ala
865                 870                 875                 880

Gly Gly Pro Tyr Thr Thr Val Ala Thr Gly Val Thr Ala Ala Gly Tyr
            885                 890                 895

Thr Asp Thr Ala Val Thr Asn Gly Thr Thr Tyr Tyr Val Val Ser
            900                 905                 910

Ala Val Asn Ala Ala Gly Glu Ser Ala Asn Ser Ala Gln Val Cys Ala
            915                 920                 925

Lys Pro Gln Ala Pro Ala Gly Thr Gly Val Val Val Leu Gln Tyr Arg
            930                 935                 940

Ala Gly Asp Thr Asn Pro Ala Asp Asn Gln Phe Lys Pro His Phe Asn
945                 950                 955                 960

Leu Val Asn Lys Gly Ser Ala Ala Val Pro Leu Ser Ser Leu Thr Ile
            965                 970                 975

Arg Tyr Trp Tyr Thr Ala Asp Ser Asp Gln Ala Leu Asn Phe Asn Val
            980                 985                 990

Asp Tyr Ala Val Val Gly Ser Ser Asn Val Thr Gly Lys Phe Val Lys
            995                 1000                1005

Leu Pro Ala Ala Arg Ser Gly Ala Asp Ser Tyr Leu Glu Val Gly
            1010                1015                1020

Phe Glu Phe Lys Pro His Phe Asn Leu Val Asn Lys Gly Ser Ala
            1025                1030                1035

Ala Val Pro Leu Ser Ser Leu Thr Ile Arg Tyr Trp Tyr Thr Ala
            1040                1045                1050

Asp Ser Asp Gln Ala Leu Asn Phe Asn Val Asp Tyr Ala Val Val
            1055                1060                1065
```

```
Gly Ser Ser Asn Val Thr Gly Lys Phe Val Lys Leu Pro Ala Ala
    1070                1075                1080

Arg Ser Gly Ala Asp Ser Tyr Leu Glu Val Gly Phe Gly Pro Gly
    1085                1090                1095

Ala Gly Ser Leu Ala Ala Gly Gly Ser Ser Gly Glu Ile Gln Thr
    1100                1105                1110

Arg Ile Asn Arg Ala Asn Trp Ser Asn Leu Ser Glu Ser Asn Asp
    1115                1120                1125

Tyr Ser Phe Asp Pro Thr Lys Thr Ala Phe Ala Asp Trp Ser Lys
    1130                1135                1140

Val Thr Val Tyr Lys Asp Gly Val Leu Ile Trp Gly Val Glu Pro
    1145                1150                1155

<210> SEQ ID NO 10
<211> LENGTH: 427
<212> TYPE: PRT
<213> ORGANISM: Unknown
<220> FEATURE:
<223> OTHER INFORMATION: GH6 cellobiohydrolase AR19G-166RA

<400> SEQUENCE: 10

Leu Asp Asn Pro Phe Ile Gly Ala Ile Gly Tyr Val Asn Pro Asp Trp
1               5                   10                  15

Ala Thr Asn Val Ile Ser Gln Ala Asn Gln Thr Ala Asp Pro Thr Leu
                20                  25                  30

Ala Ala Gln Met Arg Lys Val Ala Thr Tyr Ser Thr Ala Val Trp Leu
            35                  40                  45

Asp Arg Ile Ala Ala Ile Thr Ala Gly Arg Gly Leu Arg Gly His Leu
        50                  55                  60

Asp Glu Ala Leu Arg Gln Met Gln Gln Ala Gly Gln Pro Val Val Ile
65                  70                  75                  80

Thr Leu Val Ile Tyr Asp Leu Pro Asn Arg Asp Cys Ser Ala Ala Ala
                85                  90                  95

Ser Asn Gly Glu Leu Leu Val Ala Gln Asn Gly Leu Ala Arg Tyr Lys
                100                 105                 110

Ala Glu Phe Ile Asp Pro Ile Val Ala Ile Leu Ser Asp Pro Arg Tyr
            115                 120                 125

Ala Gly Leu Arg Ile Val Thr Ile Ile Glu Pro Asp Ser Leu Pro Asn
        130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
                180                 185                 190

Asp Asn Asn Phe Asn Gly Ala Val Asn Leu Tyr Thr Gln Val Val Gln
            195                 200                 205

Gly Met Asp Gln Gly Phe Asn Ser Ile Asp Gly Phe Ile Thr Asn Val
        210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
                260                 265                 270
```

-continued

```
Ile Gly Arg Gly Phe Pro Ser Thr Ile Gly Met Leu Ile Asp Thr Ser
        275                 280                 285

Arg Asn Gly Trp Gly Gly Cys Ser Tyr Gly Arg Cys Arg Pro Thr Gly
    290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Ala Tyr
            340                 345                 350

Val Trp Val Lys Pro Pro Gly Glu Ser Asp Gly Val Ser Gln Pro Gly
        355                 360                 365

Ile Val Asp Pro Asp Asp Pro Asn Lys Lys Phe Asp Pro Met Cys Asp
    370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
        420                 425
```

The invention claimed is:

1. An isolated recombinant thermostable cellobiohydrolase comprising a polypeptide consisting of the amino acid sequence of SEQ ID NO: 1 or 2, and
a purification tag added at the end of N-terminal or C-terminal of said polypeptide.

2. The thermostable cellobiohydrolase according to claim 1, wherein said cellobiohydrolase exhibits hydrolase activity against phosphoric acid-swollen Avicel at least under conditions of 80° C. and pH 5.5 in the presence of calcium ions.

3. A glycoside hydrolase mixture, comprising the thermostable cellobiohydrolase according to claim 1 and at least one other glycoside hydrolase.

4. The glycoside hydrolase mixture according to claim 3, further comprising a GH6 family cellobiohydrolase.

5. A method for producing a cellulose degradation product, the method comprising generating the cellulose degradation product by bringing a material containing cellulose into contact with the thermostable cellobiohydrolase according to claim 1.

6. A method for producing a cellulose degradation product, the method comprising generating the cellulose degradation product by bringing a material containing cellulose into contact with the glycoside hydrolase mixture according to claim 3.

7. The method for producing a cellulose degradation product according to claim 5, wherein the material containing cellulose is brought into contact with the thermostable cellobiohydrolase, and is also brought into contact with a GH6 family cellobiohydrolase.

8. The method for producing a cellulose degradation product according to claim 6, wherein the material containing cellulose is brought into contact with the glycoside hydrolase mixture, and is also brought into contact with a GH6 family cellobiohydrolase.

* * * * *